(12) United States Patent
Scott et al.

(10) Patent No.: US 10,821,078 B2
(45) Date of Patent: Nov. 3, 2020

(54) NANOSTRUCTURE ENHANCED TARGETING (NSET) OF INFLAMMATORY CELLS

(71) Applicant: Northwestern University, Evanston, IL (US)

(72) Inventors: Evan A. Scott, Chicago, IL (US); Sijia Yi, Evanston, IL (US); Sean D. Allen, Chicago, IL (US)

(73) Assignee: Northwestern University, Evanston, IL (US)

( * ) Notice: Subject to any disclaimer, the term of this patent is extended or adjusted under 35 U.S.C. 154(b) by 89 days.

(21) Appl. No.: 15/637,333

(22) Filed: Jun. 29, 2017

(65) Prior Publication Data

US 2018/0028446 A1 Feb. 1, 2018

Related U.S. Application Data

(60) Provisional application No. 62/357,104, filed on Jun. 30, 2016, provisional application No. 62/370,572, filed on Aug. 3, 2016.

(51) Int. Cl.
| | |
|---|---|
| *A61K 9/127* | (2006.01) |
| *A61K 47/34* | (2017.01) |
| *C08G 65/334* | (2006.01) |
| *A61K 49/00* | (2006.01) |
| *C08G 75/14* | (2006.01) |

(52) U.S. Cl.
CPC ............ *A61K 9/1273* (2013.01); *A61K 47/34* (2013.01); *A61K 49/0032* (2013.01); *A61K 49/0034* (2013.01); *A61K 49/0086* (2013.01); *C08G 65/334* (2013.01); *C08G 65/3342* (2013.01); *C08G 75/14* (2013.01); *C08G 2650/02* (2013.01)

(58) Field of Classification Search
None
See application file for complete search history.

(56) References Cited

U.S. PATENT DOCUMENTS

| | | | |
|---|---|---|---|
| 2005/0192340 A1* | 9/2005 | Flashner-Barak ... | A61K 9/4858 514/423 |
| 2015/0297711 A1* | 10/2015 | Nallani ................ | A61K 9/1273 424/400 |

OTHER PUBLICATIONS

Agyare et al. "Delivery of Polymeric Nanoparticles to Target Vascular Diseases", J Biomol Res Ther. Author manuscript; available in PMC Jun. 9, 2015 (Year: 2015).*
Charo et al. "Anti-inflammatory therapeutics for the treatment of atherosclerosis" Nat Rev Drug Discov. May 2011 ; 10(5): 365-376 (Year: 2011).*
Allen, S., et al., Engineering nanomaterials to address cell-mediated inflammation in atherosclerosis. Regen Eng Transl Med, 2016. 2(1): p. 37-50.
Alitalo, K., The lymphatic vasculature in disease. Nat Med, 2011. 17(11): p. 1371-80.
Bobryshev, Y.V., Dendritic cells and their role in atherogenesis. Lab Invest, 2010. 90(7): p. 970-984.
Butcher, M.J., et al., Flow cytometry analysis of immune cells within murine aortas. J Vis Exp, 2011(53).
Cerritelli, S., et al., Aggregation Behavior of Poly(ethylene glycol-bl-propylene sulfide) Di- and Triblock Copolymers in Aqueous Solution. Langmuir, 2009. 25(19): p. 11328-11335.
Champion, J.A. et al., Role of target geometry in phagocytosis. Proceedings of the National Academy of Sciences of the United States of America, 2006. 103(13): p. 4930-4934.
Daissormont, I.T., et al., Plasmacytoid dendritic cells protect against atherosclerosis by tuning T-cell proliferation and activity. Circ Res, 2011. 109(12): p. 1387-95.
Doring, Y., et al., Auto-antigenic protein-DNA complexes stimulate plasmacytoid dendritic cells to promote atherosclerosis. Circulation, 2012. 125(13): p. 1673-83.
Duan, X. et al., Physicochemical Characteristics of Nanoparticles Affect Circulation, Biodistribution, Cellular Internalization, and Trafficking. Small, 2013. 9(9-10): p. 1521-1532.
Gao, H., et al., Mechanics of receptor-mediated endocytosis. Proc Natl Acad Sci U S A, 2005. 102(27): p. 9469-74.
Gautier, E.L., et al., Conventional dendritic cells at the crossroads between immunity and cholesterol homeostasis in atherosclerosis. Circulation, 2009. 119(17): p. 2367-75.
Geng, Y., et al., Shape effects of filaments versus spherical particles in flow and drug delivery. Nat Nanotechnol, 2007. 2(4): p. 249-55.
Getz, G.S., et al., Natural killer T cells in lipoprotein metabolism and atherosclerosis. Thromb Haemost, 2011. 106(5): p. 814-9.
Haniffa, M., et al., Human mononuclear phagocyte system reunited. Semin Cell Dev Biol, 2015. 41: p. 59-69.
Hubbell, J.A., et al., Materials engineering for immunomodulation. Nature, 2009. 462(7272): p. 449-60.
Irvine, D.J., et al., Synthetic Nanoparticles for Vaccines and Immunotherapy. Chem Rev, 2015. 115(19): p. 11109-46.
Joffre, O.P., et al., Cross-presentation by dendritic cells. Nat Rev Immunol, 2012. 12(8): p. 557-569.
Jongstra-Bilen, J., et al., Low-grade chronic inflammation in regions of the normal mouse arterial intima predisposed to atherosclerosis. J Exp Med, 2006. 203(9): p. 2073-83.
Kim, T.H., et al., Filamentous, Mixed Micelles of Triblock Copolymers Enhance Tumor Localization of Indocyanine Green in a Murine Xenograft Model. Molecular Pharmaceutics, 2012. 9(1): p. 135-143.
Kirchherr, A.-K., et al., Stabilization of Indocyanine Green by Encapsulation within Micellar Systems. Molecular Pharmaceutics, 2009. 6(2): p. 480-491.
Lobatto, M.E., et al., Atherosclerotic plaque targeting mechanism of long-circulating nanoparticles established by multimodal imaging. ACS Nano, 2015. 9(2): p. 1837-47.

(Continued)

*Primary Examiner* — James W Rogers
(74) *Attorney, Agent, or Firm* — Quarles & Brady LLP

(57) ABSTRACT

The present invention provides nanomaterials for the specific targeting of immune cells. Methods of treating cardiac disease and inflammatory disease are also described.

10 Claims, 20 Drawing Sheets
(17 of 20 Drawing Sheet(s) Filed in Color)
Specification includes a Sequence Listing.

(56) References Cited

OTHER PUBLICATIONS

Merad, M., et al., The dendritic cell lineage: ontogeny and function of dendritic cells and their subsets in the steady state and the inflamed setting. Annu Rev Immunol, 2013. 31: p. 563-604.
Mildner, A. et al., Development and Function of Dendritic Cell Subsets. Immunity, 2014. 40(5): p. 642-656.
Moon, J.J., et al., Engineering nano- and microparticles to tune immunity. Adv Mater, 2012. 24(28): p. 3724-46.
Nel, A.E., et al., Understanding biophysicochemical interactions at the nano-bio interface. Nat Mater, 2009. 8(7): p. 543-57.
Niessner, A. et al., Dendritic cells in atherosclerotic disease. Clin Immunol, 2010. 134(1): p. 25-32.
Palombo, M., et al., Pharmaceutical and toxicological properties of engineered nanomaterials for drug delivery. Annu Rev Pharmacol Toxicol, 2014. 54: p. 581-98.
Paulson, K.E., et al., Resident intimal dendritic cells accumulate lipid and contribute to the initiation of atherosclerosis. Circ Res, 2010. 106(2): p. 383-90.
Platt, C.D., et al., Mature dendritic cells use endocytic receptors to capture and present antigens. Proc Natl Acad Sci U S A, 2010. 107(9): p. 4287-92.
Racanelli, V. et al., The liver as an immunological organ. Hepatology, 2006. 43(S1): p. S54-S62.
Reizis, B., et al., Plasmacytoid Dendritic Cells: Recent Progress and Open Questions. Annual review of immunology, 2011. 29: p. 163-183.
Rossman, J.S., et al., Filamentous influenza virus enters cells via macropinocytosis. J Virol, 2012. 86(20): p. 10950-60.
Scott, E.A., et al., Dendritic cell activation and T cell priming with adjuvant- and antigen-loaded oxidation-sensitive polymersomes. Biomaterials, 2012. 33(26): p. 6211-9.
Simon, D.I. et al., Neutrophils in atherosclerosis: alarmin evidence of a hit and run? Circ Res, 2012. 110(8): p. 1036-8.
Stano, A., et al., Tunable T cell immunity towards a protein antigen using polymersomes vs. solid-core nanoparticles. Biomaterials, 2013. 34(17): p. 4339-46.
Swartz, M.A., et al., Engineering Approaches to Immunotherapy. Science Translational Medicine, 2012. 4(148): p. 148rv9-148rv9.
Swirski, F.K.et al., Leukocyte Behavior in Atherosclerosis, Myocardial Infarction, and Heart Failure. Science, 2013. 339(6116): p. 161-166.
Swirski, F.K., et al., Ly-6Chi monocytes dominate hypercholesterolemia-associated monocytosis and give rise to macrophages in atheromata. J Clin Invest, 2007. 117(1): p. 195-205.
Takeuchi, O. et al., Pattern recognition receptors and inflammation. Cell, 2010. 140(6): p. 805-20.
Tunon, M.J., et al., Liver blood flow changes during laparoscopic surgery in pigs. A study of hepatic indocyanine green removal. Surg Endosc, 1999. 13(7): p. 668-72.
Van De Broek, B., et al., Specific cell targeting with nanobody conjugated branched gold nanoparticles for photothermal therapy. ACS Nano, 2011. 5(6): p. 4319-28.
Vasdekis, A.E., et al., Precision intracellular delivery based on optofluidic polymersome rupture. ACS Nano, 2012. 6(9): p. 7850-7.
Weber, C., et al., CCL17-expressing dendritic cells drive atherosclerosis by restraining regulatory T cell homeostasis in mice. J Clin Invest, 2011. 121(7): p. 2898-910.
Weber, C. and et al., Atherosclerosis: current pathogenesis and therapeutic options. Nat Med, 2011. 17(11): p. 1410-1422.
Writing Group, M, et al., Heart Disease and Stroke Statistics—2016 Update: A Report From the American Heart Association. Circulation, 2016. 133(4): p. e38-60.
Yi, S., et al., Tailoring nanostructure morphology for enhanced targeting of dendritic cells in atherosclerosis, ACS Nano 2016, 10(12):11290-11303.
Alexis, et al., Factors Affecting the Clearance and Biodistribution of Polymeric Nanoparticles. Molecular Pharmaceutics. 2008, 5(4): 505-515.
Napoli, et al., Lyotropic Behavior in WAter of Amphiphilic ABA Triblock Copolymers Based on Poly(propylene sulfide) and Poly(ethylene glycol). American Chemical Society. 2002, 18: 8324-329.
Owen, et al., Polymeric micelle stability. Nano Today. 2012, 7: 53-65.

* cited by examiner

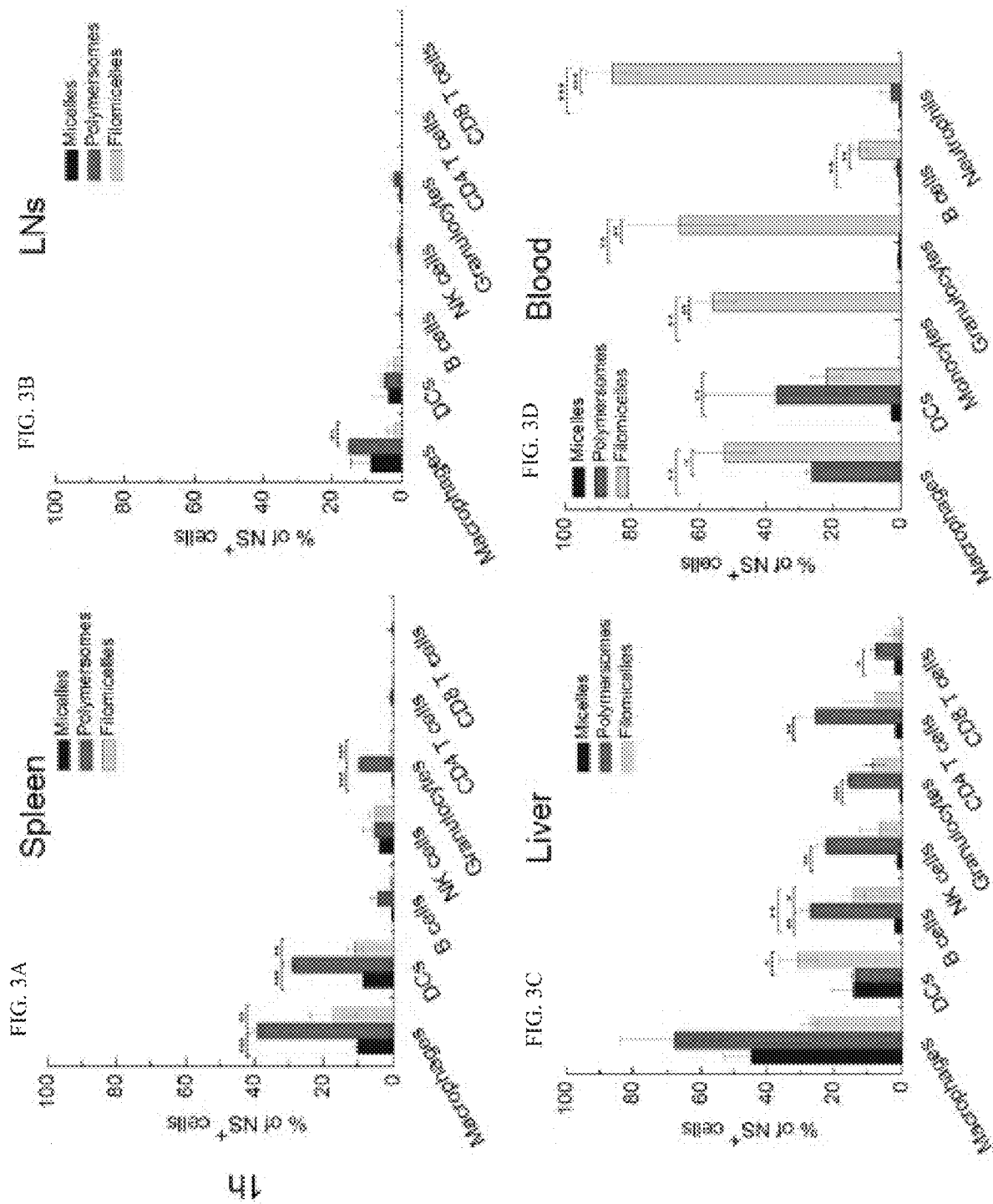

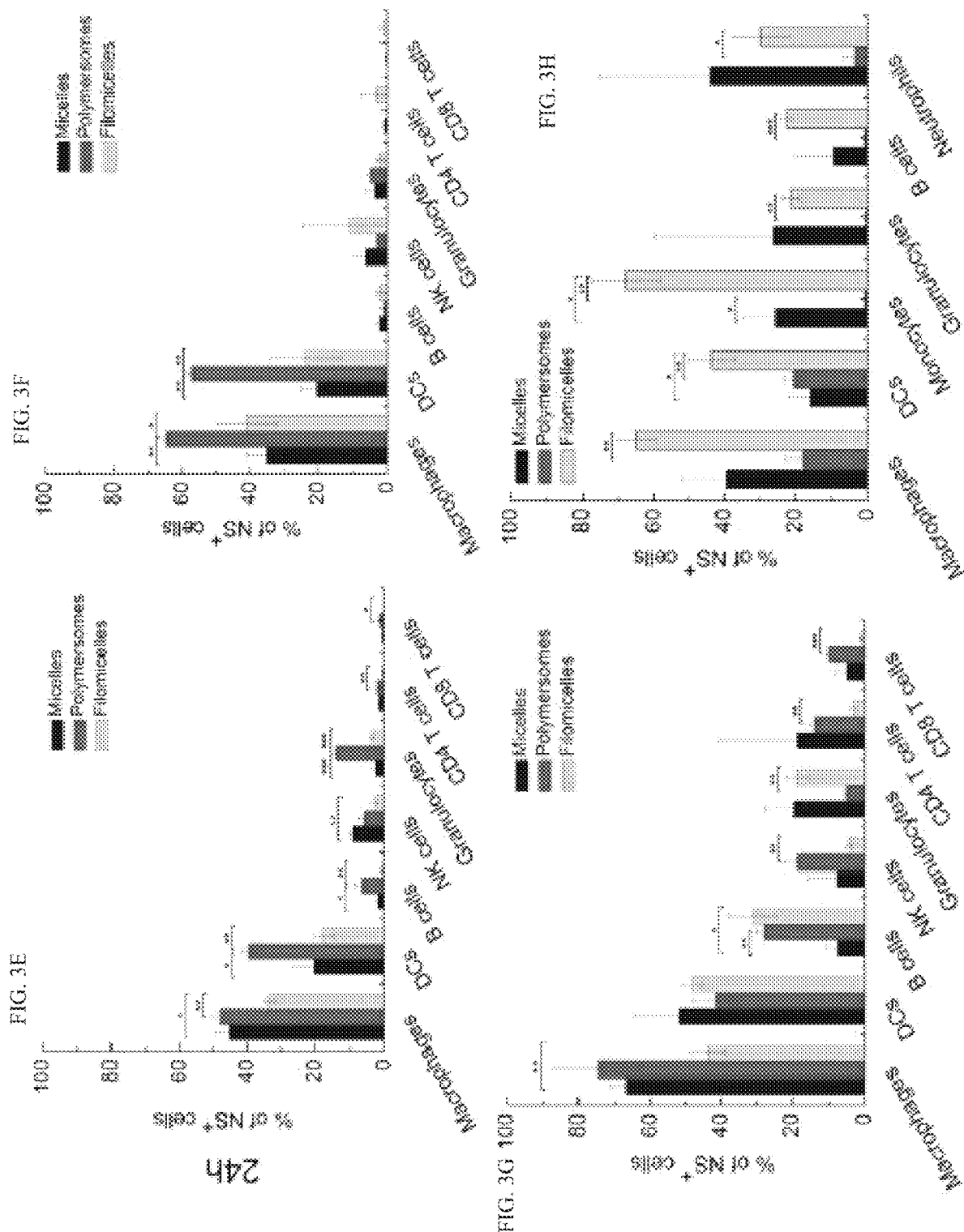

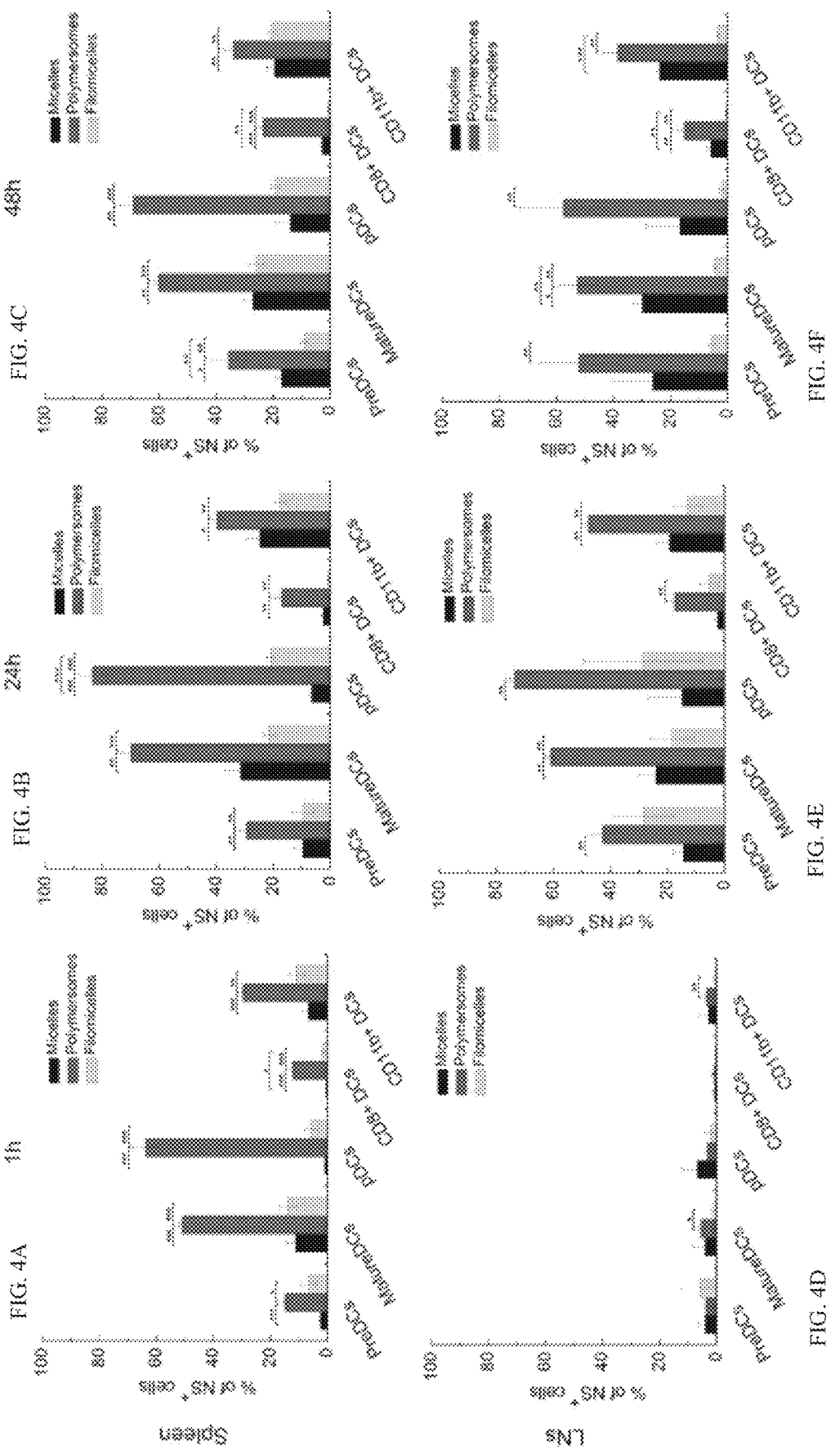

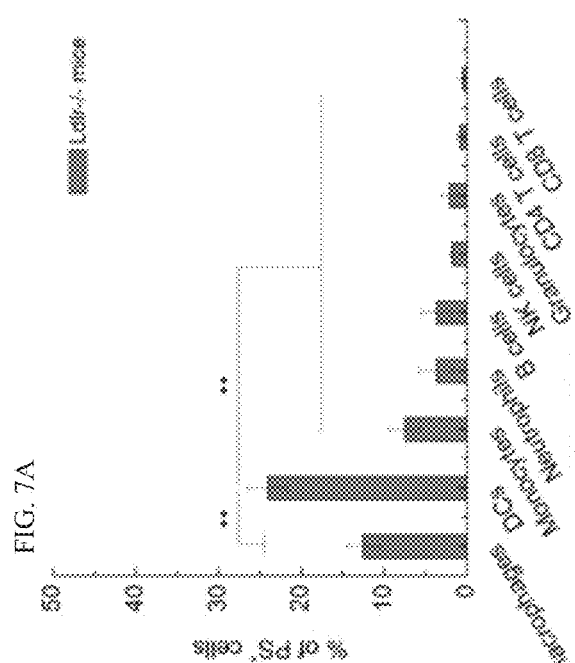
FIG. 7A
FIG. 7B
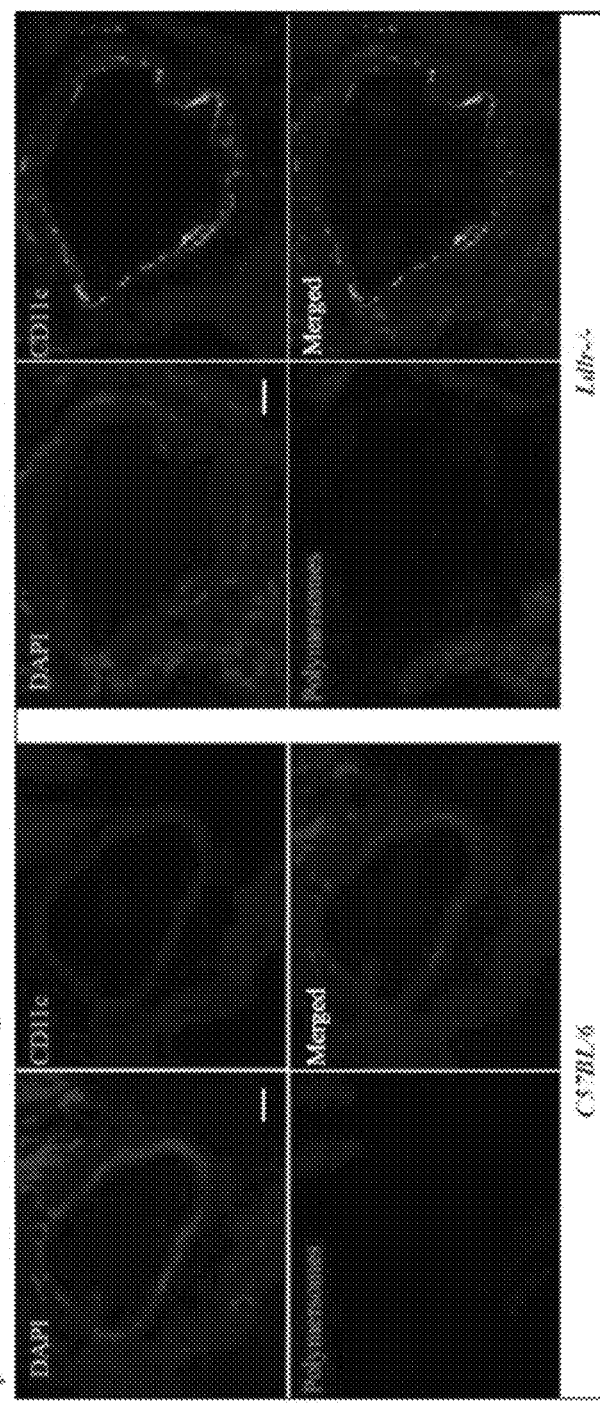
FIG. 7C

NANOSTRUCTURE ENHANCED TARGETING (NSET) OF INFLAMMATORY CELLS

CROSS-REFERENCE TO RELATED APPLICATIONS

This application claims priority to U.S. Provisional Application No. 62/357,104 filed on Jun. 30, 2016 and 62/370,572 filed on Aug. 3, 2016, the contents of which are incorporated by reference in their entireties.

STATEMENT REGARDING FEDERALLY SPONSORED RESEARCH

This invention was made with government support under HL132390 awarded by the National Institutes of Health. The government has certain rights in the invention.

BACKGROUND OF THE INVENTION

An unsolved challenge for the controlled delivery of therapeutics is non-specific cellular uptake by the mononuclear phagocytes system (MPS), which consists of phagocytic cells in the liver, spleen, lymph nodes (LN), kidneys and blood [1]. These monocytes, macrophages, and dendritic cells (DC) readily clear nanomaterials from the circulatory system regardless of their engineered surface chemistries or targeting ligands, which can result in decreased efficacy and adverse effects [2]. Certain populations of MPS cells serve as professional antigen presenting cells (APC), which process and present nano- and microscale pathogens for the generation of controlled inflammatory and immune responses. The function and inflammatory potential of each APC subset is distinct, and differences in preferred mechanisms of uptake, surface receptor concentration as well as organ location contribute to the efficiency of pathogen and nanomaterial endocytosis and the resulting generation of directed immune responses [3-5]. All of these factors can be influenced by nanostructure morphology, i.e. the geometry (size, shape and aspect ratio), which can determine cell membrane interactions, transport through biological fluids and tissues, circulation time and intracellular delivery [6-8].

Atherosclerosis is an inflammatory condition within the walls of arterial vessels and a principal cause of cardiovascular disease (CVD). Accumulation of inflammatory cells and their products induce maturation of atheromas, or plaques, ultimately resulting in plaque rupture, leading to ischemic stroke or myocardial infarction [12]. Since monocytes and macrophages are primary mediators of lipid accumulation within arterial vessel walls, they have become the focus of targeted delivery for imaging and treatment of atherosclerosis [11]. However, atherosclerotic lesions contain a complex mixture of diverse immune cell populations, including T cells, neutrophils, eosinophils and DC [13-15]. Activated by a uniquely diverse range of pattern recognition receptors [16], DC progress from preDC precursors to mature DC, which are marked by heightened expression of cytokines, chemokines and cell surface coreceptors that activate diverse T cell subsets and drive atherosclerotic inflammation. DC are found within atheromas at all stages of lesion development, and although their accumulation correlates with the level of plaque instability, they have been found to be both atherogenic as well as atheroprotective, likely a result of their heterogeneity [17-21]. Much attention has been generated for the targeting of DC in cancer immunotherapies [10, 22, 23], but few therapeutic strategies have focused on targeting these cells in CVD.

SUMMARY OF THE INVENTION

Nanomaterials are versatile platforms for diagnostic imaging and controlled delivery of therapeutics, but efficacy is limited by non-specific uptake and systemic clearance by cells of the mononuclear phagocytes system. Applicant hypothesized that nanostructure morphology may be engineered for selective uptake by distinct inflammatory cell populations within the MPS. By mimicking the distinct nanostructures (NS) of viruses while maintaining the same surface chemistry, different MPS cell populations could be targeted by nanomaterials to different degrees without the use of a targeting ligand. Enhanced targeting of specific MPS subsets by nanomaterials may decrease off-target effects of drug therapy, improve targeted immunotherapy and offer new treatments for inflammation-driven pathologies like CVD [9-11].

Employing near infrared fluorescence imaging and flow cytometry as a multimodal approach, Applicant compared organ- and cellular-level biodistributions of micelles, vesicles (i.e. polymersomes) and filomicelles, all with identical surface chemistries. Polymersomes were identified for enhanced uptake by dendritic cells (DC), which are critical mediators of inflammation and targets for immunotherapy and vaccination. In a mouse model of atherosclerosis, a chronic vascular inflammatory disease, significant differences in polymersome biodistribution were observed relative to naïve mice. Importantly, polymersomes demonstrated superior specificity for therapeutically relevant subsets of DC in both spleen and atherosclerotic lesions without the need for targeting ligands, presenting new avenues for immunotherapies in cardiovascular disease.

In one aspect, the disclosure provides a polymersome comprising a vesicular polymer membrane comprising block copolymers of poly(ethylene glycol) (PEG) and poly(propylene sulfide) (PPS) for targeting uptake of the polymersome to a cell, preferably dendritic cells.

In another aspect, the disclosure provides a method of targeting an agent to dendritic cells comprising incorporating or encapsulating the agent in a polymersome.

In a further aspect, the disclosure provides a method of treating cardiovascular disease comprising targeting polymersomes to dendritic cells associated with cardiovascular disease in a subject, wherein the polymersomes incorporate, encapsulate, and/or deliver a therapeutic agent able to treat CVD.

In yet another aspect, the disclosure provides a method of imaging dendritic cells associated with an inflammatory response in a subject, the method comprising administering polymersomes comprising a diagnostic agent to the subject. In some aspects, the diagnostic agent is an imaging agent. In some aspects, the polymersomes comprise block copolymers of poly(ethylene glycol) (PEG) and poly(propylene sulfide) (PPS), and wherein the polymersomes are selectively taken up by dendritic cells.

An advantage of the polymersomes of embodiments of the present disclosure is that they selectively target dendritic cells without the use of targeting ligands.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A Assessment of cellular-level biodistributions of PEG-bl-PPS nanostructures. Flow cytometric analysis of the association of MC, PS and FM with immune cells isolated from spleen of C57BL/6 mice after time points of 1 h following tail vein injection. Histograms show the average percentages±standard deviation (SD) of each indicated cell type that was nanostructure positive (NS+). Macrophages: $CD11b^+F4/80^+$; dendritic cells (DCs): $CD11c^+$; B cells: $CD45^+CD19^+$; natural killer (NK) cells: $CD45^+CD49b^+$; granulocytes: $Gr-1^+CD11b^+$; CD4 T cells: $CD45^+CD3^+CD4^+$; CD8 T cells: $CD45^+CD3^+CD8^+$. Refer to gating strategies in FIG. 11. N=3 in each group, two independent experiments. Statistical significance: *$p≤0.01$, $p≤0.005$, *$p≤0.0001$.

FIG. 3B Flow cytometric analysis of the association of MC, PS and FM with immune cells isolated from lymph nodes of C57BL/6 mice after time points of 1 h following tail vein injection. Histograms show the average percentages±standard deviation (SD) of each indicated cell type that was nanostructure positive (NS+). Cells same as in FIG. 3A. N=3 in each group, two independent experiments. Statistical significance: *$p≤0.01$, $p≤0.005$, *$p≤0.0001$.

FIG. 3C Flow cytometric analysis of the association of MC, PS and FM with immune cells isolated from liver of C57BL/6 mice after time points of 1 h following tail vein injection. Histograms show the average percentages±standard deviation (SD) of each indicated cell type that was nanostructure positive (NS+). Cells same as in FIG. 3A. N=3 in each group, two independent experiments. Statistical significance: *$p≤0.01$, $p≤0.005$, *$p≤0.0001$.

FIG. 3D Flow cytometric analysis of the association of MC, PS and FM with immune cells isolated from blood of C57BL/6 mice after time points of 1 h following tail vein injection. Histograms show the average percentages±standard deviation (SD) of each indicated cell type that was nanostructure positive (NS+). Cells same as in FIG. 3A. N=3 in each group, two independent experiments. Statistical significance: *$p≤0.01$, $p≤0.005$, *$p≤0.0001$.

FIG. 3E Flow cytometric analysis of the association of MC, PS and FM with immune cells isolated from spleen of C57BL/6 mice after time points of 24 h following tail vein injection. Cells same as in FIG. 3A. N=3 in each group, two independent experiments. Statistical significance: *$p≤0.01$, $p≤0.005$, *$p≤0.0001$.

FIG. 3F Flow cytometric analysis of the association of MC, PS and FM with immune cells isolated from lymph nodes of C57BL/6 mice after time points of 24 h following tail vein injection. Histograms show the average percentages±standard deviation (SD) of each indicated cell type that was nanostructure positive (NS+). Cells same as in FIG. 3A. N=3 in each group, two independent experiments. Statistical significance: *$p≤0.01$, $p≤0.005$, *$p≤0.0001$.

FIG. 3G Flow cytometric analysis of the association of MC, PS and FM with immune cells isolated from liver of C57BL/6 mice after time points of 24 h following tail vein injection. Histograms show the average percentages±standard deviation (SD) of each indicated cell type that was nanostructure positive (NS+). Cells same as in FIG. 3A. N=3 in each group, two independent experiments. Statistical significance: *$p≤0.01$, $p≤0.005$, *$p≤0.0001$.

FIG. 3H Flow cytometric analysis of the association of MC, PS and FM with immune cells isolated from blood of C57BL/6 mice after time points of 24 h following tail vein injection. Histograms show the average percentages±standard deviation (SD) of each indicated cell type that was nanostructure positive (NS+). Cells same as in FIG. 3A. N=3 in each group, two independent experiments. Statistical significance: *$p≤0.01$, $p≤0.005$, *$p≤0.0001$.

FIG. 4A Biodistributions of MC, PS and FM in dendritic cell subsets from spleen after 1 h following I.V. injection analyzed by flow cytometry. Histograms show the average percentages±standard deviation (SD) of each indicated cell type that was nanostructure positive (NS$^+$). Definitions: PreDC: I-A/I-E-CD11c+; mature DCs: I-A/I-E$^+$CD11c$^+$; plasmacytoid DCs: I-A/I-E$^+$CD11c$^+$Gr-1$^+$B220$^+$; CD8$^+$ DCs: I-A/I-E$^+$CD11c$^+$CD8$^+$; CD11b$^+$ DCs: I-A/I-E$^+$CD11c$^+$CD11b$^+$ which are applicable to 4B-4F below. N=3 in each group, two independent experiments. Statistical significance: *p≤0.01, p≤0.005, *p≤0.0001.

FIG. 4B Biodistributions of MC, PS and FM in dendritic cell subsets from spleen after 24 h following I.V. injection analyzed by flow cytometry. Histograms show the average percentages±standard deviation (SD) of each indicated cell type that was nanostructure positive (NS$^+$). N=3 in each group, two independent experiments. Statistical significance: *p≤0.01, p≤0.005, *p≤0.0001.

FIG. 4C Biodistributions of MC, PS and FM in dendritic cell subsets from spleen after 48 h following I.V. injection were analyzed by flow cytometry. Histograms show the average percentages±standard deviation (SD) of each indicated cell type that was nanostructure positive (NS$^+$). N=3 in each group, two independent experiments. Statistical significance: *p≤0.01, p≤0.005, *p≤0.0001.

FIG. 4D Biodistributions of MC, PS and FM in dendritic cell subsets from LNs after 1 h following I.V. injection were analyzed by flow cytometry. Histograms show the average percentages±standard deviation (SD) of each indicated cell type that was nanostructure positive (NS$^+$). N=3 in each group, two independent experiments. Statistical significance: *p≤0.01, p≤0.005, *p≤0.0001.

FIG. 4E Biodistributions of MC, PS and FM in dendritic cell subsets from LNs after 24 h following I.V. injection were analyzed by flow cytometry. Histograms show the average percentages±standard deviation (SD) of each indicated cell type that was nanostructure positive (NS$^+$). N=3 in each group, two independent experiments. Statistical significance: *p≤0.01, p≤0.005, *p≤0.0001.

FIG. 4F Biodistributions of MC, PS and FM in dendritic cell subsets from LNs after 48 h following I.V. injection were analyzed by flow cytometry. Histograms show the average percentages±standard deviation (SD) of each indicated cell type that was nanostructure positive (NS$^+$). N=3 in each group, two independent experiments. Statistical significance: *p≤0.01, p≤0.005, *p≤0.0001.

FIG. 7A Distribution of PS within immune cell populations in the aortas of atherosclerotic (Ldlr$^{-/-}$) mice at 24 h post-injection, as analyzed by flow cytometry. Definitions: Macrophages: CD11b$^+$F4/80$^+$; DC: CD11c$^+$; B cells: CD45$^+$CD19$^+$; NK cells: CD45$^+$CD49b$^+$; granulocytes: Gr-1$^+$CD11b$^+$; CD4 T cells: CD45$^+$CD3$^+$CD4$^+$; CD8 T cells: CD45$^+$CD3$^+$CD8$^+$. N=3 for each group, two independent experiments. Statistical significance: **p≤0.005.

FIG. 7B Spinning disk confocal fluorescence images (Z-stacks) of aortic tissue from an Ldlr$^{-/-}$ mouse after I.V. injection of Dylight 650-labeled PS 24 h prior to excision. The nuclei were stained with DAPI (Blue); DCs were stained with Alexa 488 dye conjugated to anti-CD11c antibody (Green); Dylight 650-labeled PS (Red). Scale bar, 10 µm.

FIG. 7C Confocal immunofluorescence images of aortas from C57BL/6 mice and Ldlr$^{-/-}$ mice following I.V. injection of PS-Dylight650 (Red) 24 h prior to excision. Serial cross-sections (5 µm thickness) were stained with DAPI (Blue), and Alexa 488 dye conjugated antibodies against CD11c (Green) for detection of DC. Scale bar=50 µm.

DETAILED DESCRIPTION OF THE INVENTION

Figure 1C:
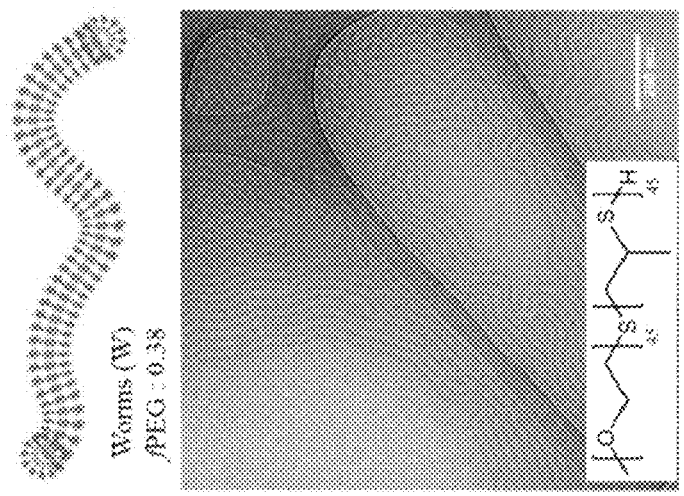
FIG. 1C Nanostructure morphologies assembled from $PEG_{44}$-bl-$PPS_{45}$ filomicelles (FM) (scale bar=200 nm) were imaged by CryoTEM. The chemical structure of each copolymer is inserted into the lower left corner of the images. The hydrophilic PEG fraction (fPEG) of the total block copolymer molecular weight and assembled nanostructure morphology are shown above each CryoTEM image.

The present invention has been described in terms of one or more preferred embodiments, and it should be appreciated that many equivalents, alternatives, variations, and modifications, aside from those expressly stated, are possible and within the scope of the invention.

Nanomaterials are versatile platforms for diagnostic imaging and controlled delivery of therapeutics, but efficacy is limited by non-specific uptake and systemic clearance by cells of the mononuclear phagocytes system. Embodiments of the present invention provide polymersomes for enhanced uptake by dendritic cells which are critical mediators of inflammation and targets for immunotherapy and vaccination. In a mouse model of atherosclerosis, a chronic vascular inflammatory disease, significant differences in polymersome biodistribution were observed relative to naïve mice. Polymersomes of embodiments of the present invention demonstrated superior specificity for therapeutically relevant subsets of DC in both spleen and atherosclerotic lesions without the need for targeting ligands, presenting new systems for delivery of immunotherapies in cardiovascular disease and other inflammatory-driven pathologies. Suitably, the polymersomes of the present invention may be used for diagnostics, for example, identifying unstable atherosclerotic plaques for early detection of heart disease, delivery of MRI contrast agents, delivery of fluorescent imaging agents, delivery of radiocontrast agents, and the like. Suitably the polymersomes of embodiments of the present invention may also be used for therapeutics, for example, delivery of anti-inflammatory agents, delivery of chemotherapeutics, delivery of statins, delivery of siRNA/micriRNA/plasmids, delivery of vaccine formulations, and delivery of inflammatory agents to probe cell function in situ, and the like.

The present disclosure is directed to nanostructure-enhanced targeting (NSET) of DC relative to other MPS cells, and improved targeting of DC in atherosclerosis. Applicant synthesized ~20 nm micelles (MC), ~100 nm polymersomes (PS), and ~50 nm×micron length filomicelles (FM) using the same block copolymer chemistry. The organ and cellular biodistributions of each morphology was respectively assessed by near infrared florescence (NIRF) imaging and flow cytometry following intravenous (I.V.) injection into normal C57BL/6 mice. PS were the only nanostructure found to consistently associate with a higher percentage of DC relative to other MPS cells. Applicant therefore selected PS for further investigation as a vehicle to target both splenic and atheroma-resident DC in an Ldlr−/− mouse model of atherosclerosis. In both locations Applicant observed significantly higher percentages of DC that were positive for PS relative to other MPS cell populations. Furthermore, Applicant observed significantly decreased uptake of PS by lymph node resident DC, which may have important implications for the application of immunotherapeutic strategies under conditions of atherosclerosis or high fat diets. These results open new avenues for therapeutic intervention of atherosclerotic inflammation by modulating DC and suggest that NSET warrants further investigation for improved nanomaterial targeting.

The present polymersomes provide lower cost options for targeting immune cells, as they do not require antibodies or surface conjugated ligands and there are high throughput methods available for rapid assembly and loading of nanomaterials. Further the polymersomes can be used for highly specific targeting, as they are able to target key inflammatory cells with lower interference from the MPS, have a lower targeting to nonspecific cells, leading to decreased side effects and toxicity of chemotherapy and allows for targeting of cells in heart disease that have not been targeted previously (dendritic cells).

NSET involves the selection of an appropriate nanostructure aspect ratio, size, surface stiffness and shape to enhance the targeting of specific cells while decreasing nonspecific uptake by others. Self-assembling block copolymers allow the controlled assembly of these different structures to influence cell uptake and targeting.

Prior methods of targeting use surface functionalization, wherein surfaces of nanomaterials are conjugated to targeting ligands or antibodies. This drastically increases the cost of the system while only minimally enhancing targeting (typically by 1%-5%) since surface modification does not inhibit nonspecific uptake by phagocytic cells in the spleen, kidneys, liver, blood, and lymph nodes. Changing the nanostructure to polymersomes drastically increases uptake of these cells (by up to 50%) without the need for costly surface modifications. The polymersomes of the present invention allow an increased uptake specifically to dendritic cells. These polymersomes along with having an increased uptake specifically to dendritic cells in all organs including within atheromas also have a decrease in uptake by monocytes and macrophages.

In some embodiments, the present polymersomes increase the specific uptake of an agent by dendritic cells by at least 20%, alternatively by at least 30%, alternatively by at least 40%, alternatively by at least 50%.

In some embodiments, the present polymersomes have a decrease in uptake by monocytes and macrophages by at least 10%, alternatively at least 20%, alternatively at least 30%, alternatively at least 40% decreased uptake by monocytes as compared to micelles.

The polymersomes of the present invention also can reduce side effects of drugs, e.g. chemotherapeutic agents, due to poor targeting of drugs and nanocarriers and non-specific uptake. The polymersomes reduce non-specific targeting which in turn decreases many if not substantially all drug-related side effects.

The polymersomes further are versatile in the ability to load and deliver diverse therapeutics, controllable release mechanisms, and intracellular delivery for gene therapy.

In one embodiment, a polymersome comprising a vesicular polymer membrane comprising block copolymers of poly(ethylene glycol) (PEG) and poly(propylene sulfide) (PPS) for targeting uptake of the polymersome into a dendritic cell. Suitably, the size of the polymersome is about 90 nm to about 150 nm in diameter, alternatively from about 100 nm to about 150 nm, alternatively from about 100 nm to about 120 nm in diameter. In one embodiment, the polymersomes comprise vesicular polymer membrane is $PEG_{17}$-bl-$PPS_{30}$. An advantage of the polymersomes of the present invention is they can target dendritic cells and immune cells without the use of a targeting ligand.

The polymersomes may be used as described in Allen et al. Regen. Eng. Transl. Med., 2016, which is incorporated by reference in its entirety.

In one embodiment, the polymersomes of the present invention may be used for diagnostics. In one example, polymersomes may be used to identify unstable atherosclerotic plaques for early detection of heart disease, delivery of MRI contrast agents, delivery of fluorescent imaging agents, delivery of radiocontrast agents, and the like.

The polymersomes of the present invention can be used to diagnose any disorder involving abnormal locations or number of inflammatory cells. For example, but not limited to, the polymersomes may be able to detect atherosclerotic plaques, tumors, tumor metastasis, damaged vasculature from multiple disorders and the like.

The polymersome in some embodiments include a diagnostic agent comprising at least one visible or near infrared-emissive agent that is dispersed within the polymersome membrane. For example, NIR fluorophores (NIRFs) may be incorporated into the polymersomes. Suitable NIR agents include, but are not limited to, phthalocyanines, cyanine dyes and squaraine dyes and the like. Other visible emissive agents include, but are not limited to, indocyanine, fluorescein, and the like. Any suitable fluorophore that is soluble in water, ethanol, DMF, THF, DCM or DMSO is able to be incorporated into the polymersomes of the present invention.

The polymersomes may be used to deliver MRI contrast agents, for example, suitable MRI contrast agents include, but are not limited to, gadolinium-based agents, for example, gadoterate (Dotarem. Clariscan), gadodiamide (Omniscan), gadobenate (MultiHance), gadopentetate (Magnevist), gadoteridol (ProHance), gadoversetamide (OptiMARK), gadobutrol (Gadovist [EU]/Gadavist [US]), gadopentetic acid dimeglumine (Magnetol), albumin-binding gadolinium complexes, for example, gadofosveset, gadocoletic acid, and polymeric gadolinium complexes, for example, gadomelitol, gadomer 17, iron oxide including, for example, superparamagnetic iron oxide (SPI)) and ultrasmall superparamagnetic iron oxide (USPIO), for example Ferumoxisil, Ferristene, ferric ammonium citrate, iron platinum particles (SIPPs), manganese nanoparticles, perflubron, any chemical derivatives of one of these molecules, and the like.

The polymersomes may be used to deliver radiocontrast agents. Suitable radiocontrast agents can include, but are not limited to, agents that contain barium or iodine, and the like. Iodine containing contrast agents can be ionic or non-ionic. Suitable examples of ionic iodine radiocontrast agents include, but are not limited to, for example, diatrizoate (diatrixoic acid), metrizoate (metrizoic acid), iothalamate, ioxaglate, iodamide, iotalamic acid, ioxitalamic acid, ioglicic acid, acetrizoic acid, iocarmic acid, methiodal, diodone, calcium iopodate, sodium iopodate, adipiodone, ioglycamic acid, ethyl esters of iodised fatty acids, for example, iopydol, propyliodone, iofendylate, lipiodol, and the like. Suitable non-ionic iodine radiocontrast agents include, but are not limited to, for example, iopamidol, iohexol, ioxilan, iopromide, iodixanol, ioversol and the like. Suitable barium containing radiocontrast agents include barium sulfate. Other contrasts agents include, for example, thorium dioxide.

It has become increasingly important to detect the stage of atherosclerosis lesions and cardiac disease in order to accurately assess disease state. There are a number of imaging technologies currently used clinically to image atherosclerotic plaques, namely, positron emission tomography (PET), X-ray computed tomography (CT), near-infrared fluorescence (NIRF), and magnetic resonance imaging (MRI). The polymersomes of the present invention may be used to enhance these techniques for imagining atherosclerotic plaques and in determining the disease state. In some embodiments, the imaging techniques may be combined, for example, PET-CT, PET-MRI and MRI-NIRF, and the like.

In some embodiments, the polymersomes can be used for therapeutics. In one embodiment, the polymersomes may be used for delivery of anti-inflammatory agents, delivery of chemotherapeutics, delivery of statins, delivery of siRNA/micriRNA/plasmids (e.g. gene therapy), delivery of vaccine formulations, and delivery of inflammatory agents, and the like, and can be used to probe cell function in situ.

Suitably, the polymersomes may be used to deliver gene therapy. For example, the polymersomes may be used to deliver nucleic acids to modulate the expression of inflammatory mediators, either through transient modulation or permanent gene therapy. For this, delivery of nucleic acids to target cells is required. The present polymersomes allow for delivery of nucleic acids to target cells, thus allowing the nucleic acids to reach their target before degradation in the extracellular space by nucleases or low tissue penetration. Since nucleic acids are difficult to functionalize with targeting moieties and are poorly endocytosed by cells, the use of the polymersomes allows for targeted delivery and improved uptake.

In some embodiments, the polymersomes are used to carry small interfering (siRNA) to dendritic cells. Specifically, siRNAs that can modulate the expression of immune factors is contemplated. In one example, the polymersomes may carry siRNA specific to IL-1, TNF, IL-6, IL-12, IL-23, IL-10, Type I and Type II interferons, or netrin-1, and the like. Not to be bound by any theories, but netrin-1 is important for macrophage migration and the treatment of atheromas. In one embodiment, these siRNA's are used to reduce inflammation within atheromas. In some embodiments, the siRNA is specific to downregulate inflammatory markers. In one embodiment, the siRNA may target IL-2 or TNF-$\alpha$. For example, in one embodiment, siRNA targeting mitogen-activated protein kinase kinase kinase kinase 4 (Map4k4) may be used to reduce TNF-$\alpha$ and IL-1$\beta$.

In some embodiments, the polymersomes are used to target in vivo delivery of microRNA mimics (miRNA or miR) and anti-miRNA (antagomir or antimir). For example, in one embodiment, the encapsulated miRNA-181b mimics or miR-155 can be systemically delivered to treat or prevent atherosclerosis. Administration of miRNA may result in a reduction or inhibition of atherosclerotic plaques. The ability to specifically target dendritic cells allows for the avoidance of off-target effects following systemic administration, allowing for more specific treatment and increase in positive outcomes. Other suitable miRNA for treatment of atherosclerosis include, but are not limited to, for example, miR-155, miRNA-146a, miRNA-341-5p, and the like. Suitable miRNAs may be known in the art. miRNAs or siRNAs may be specific to target atherosclerotic inflammation, including inflammation within the vascular endothelium.

The polymersomes of some of the embodiments of the present invention can be used to load plasmids and proteins simultaneously. For example, the polymersomes may be used to load CRISPR/Cas 9.

In some embodiments, the polymersomes may be used to deliver siRNA against VE-cadherin to activated endothelial cells in vivo or smooth muscle cells in vivo, for example, antagomir to miR-92a may be used to reduce endothelial inflammation or reduce plaque size of atherosclerotic plaques.

In some embodiments, the polymersomes may be used to deliver immunotherapy against atherosclerosis specifically targeted to dendritic cells. Dendritic cells play a complex role in atherosclerosis depending on their subset, as some are proatherogenic and others atheroprotective. Phasmacytoid DCs (pCDs) have a particularly dichotomous role, serving as the primary source of proatherogenic type I interferon (IFN) while also playing key roles in the activation of regulator T cells (Tregs) that stabilize plaques and prevent rupture. Inflammation induced by pDCs promotes atherosclerosis through mechanisms that involve natural killer T (NKT) cells. Thus, the polymersomes of the present invention may be used to target immune cell components of atherosclerosis by inducing tolerance and reducing the immune response within atherosclerotic plaques. For example, polymersomes may be used to deliver atheroprotective vaccination or immunotherapies.

In some embodiments, the polymersomes may be used to deliver peptides derived from ApoB-100, including, but not limited to, for example, P2(TRFKHLRKY-TYNYEAESSS (SEQ ID NO:1)), P143(IALDDAKINFNEKLSQLQTY (SEQ ID NO:2)), and P210(KTTKQSFDLSVKAQYK-KNKH (SEQ ID NO:3). In some embodiments, suitable antigenic peptides may come from oxidized lipoproteins, like ox-LDL.

In some embodiments, the polymersomes may be used to deliver a vaccine against heart disease. In one embodiment, the vaccine may be to antigens within oxidized LDL (ox-LDL), primarily oxidized phospholipids and peptide fragments of apoB-100 and the like. Other suitable targets for use in vaccines delivered via polymersomes are plasmids targeting cholesteryl ester transfer protein (CEPT), HB-ATV--8, native LDL or LDL-derived peptides, and the like.

In some embodiments, the methods of treating cardiac disease or treating atherosclerosis include enhancing the delivery of statins. Statins not only hinder cholesterol biosynthesis and Rho-associated kinase (ROCKs) activity, statins also decrease cell-mediated inflammation by inhibiting 3-hydroxy-3-methylglutaryl-coenzyme-A (HMG-CoA) reductase. There are benefits to targeting statins via polymersomes to better target plaque-resident inflammatory cells as well as minimize toxic side effects in the liver. Not to be bound by theory, delivery of statins directly to immune cells within atherosclerotic plaques can reduce progression of plaque inflammation as well as decrease inflammation in advanced atheromas.

In addition, the polymersomes may be used to deliver other immune modulators directly to atherosclerotic plaques.

In some embodiments, the therapeutic agent is an agent for treating cardiovascular disease, including, for example, treating atherosclerotic plaques. In some embodiments, the therapeutic agent is an agent that treats, reduces or inhibits atherosclerotic lesions. In some embodiments, the therapeutic agent for treating cardiovascular disease is a statin. In another embodiment, the therapeutic agent is an agent that can increase macrophage migration, as egress of macrophages can remove lipid from plaques. For example, in one embodiment, the therapeutic agent may be an siRNA targeted to the netrin-1 gene, or a plasmid expressing the netrin-1 gene.

By "treat" or "treating" we mean reduce one or more symptoms associated with the disease or disorder, for example, for atherosclerosis, treating may reduce or inhibit the formation of atherosclerotic lesions, e.g. as seen by a reduction in size or thickness of atherosclerotic plaques.

In some embodiments, the therapeutic agent is an agent that treats, reduces or inhibits lesions in the spleen.

In other embodiments, the therapeutic agent is an agent for treating chronic vascular inflammatory disease. In one example, the therapeutic agent is a statin. Different types of statins are contemplated for use in the present technology, including, for example, fermentation-derived and synthetic statins. Suitable statins may include, but are not limited to, atorvastatin (Lipitor®), fluvastatin (Lescol®, LescolXL®), lovastatin (Mevacor, Altoprev), pravastatin (Pravachol), rosuvastatin (Crestor), simvastatin (Zocor), and pitavastatin (Livalo), mevastatin (Compactin), niacin extended-release, among others. In some embodiments, the polymersomes target the dendritic cells are associated with an inflammatory response in a subject. When the inflammatory response is associated with cardiovascular disease in a subject, the polymersomes target a therapeutic agent to treat the cardiovascular disease.

In one embodiment, the method of treating cardiovascular disease comprises targeting a polymersome to a dendritic cell associated with cardiovascular disease in a subject, wherein the polymersome incorporates, encapsulates, or otherwise delivers, a therapeutic agent able to treat cardiovascular disease. In some aspects, the polymersome comprises a vesicular polymer membrane comprising block copolymers of poly(ethylene glycol) (PEG) and poly(propylene sulfide) (PPS), wherein the size of the polymersome is about 90 to about 150 nm in diameter, and wherein the therapeutic agent is delivered to dendritic cells within the subject and ameliorates at least one symptom of cardiovascular disease.

In some embodiments, the cardiovascular disease comprises atherosclerotic lesions. The therapeutic agent is a therapeutic agent that treats, reduces or inhibits atherosclerotic lesions in the subject. In some aspects, the therapeutic agent is an immunotherapy or gene therapy agent.

In some embodiments, the invention provides a method of imaging a dendritic cell associated with an inflammatory response in a subject, the method comprising administering polymersomes comprising a diagnostic agent to the subject, wherein the diagnostic agent is an imaging agent, and wherein the polymersomes comprise block copolymers of poly(ethylene glycol) (PEG) and poly(propylene sulfide) (PPS), and wherein the polymersomes are selectively taken up by dendritic cells. In some embodiments, the imaging agent is, for example, one or more of a MRI contrast agent, fluorescent imaging agent, and radiocontrast agent, and the like. In a preferred embodiment, the polymersome comprises a vesicular polymer membrane comprising $PEG_{17}$-bl-$PPS_{30}$.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Results and Discussion

Fabrication and Characterization of PEG-bl-PPS Nanostructure Morphologies

Figure 1B:
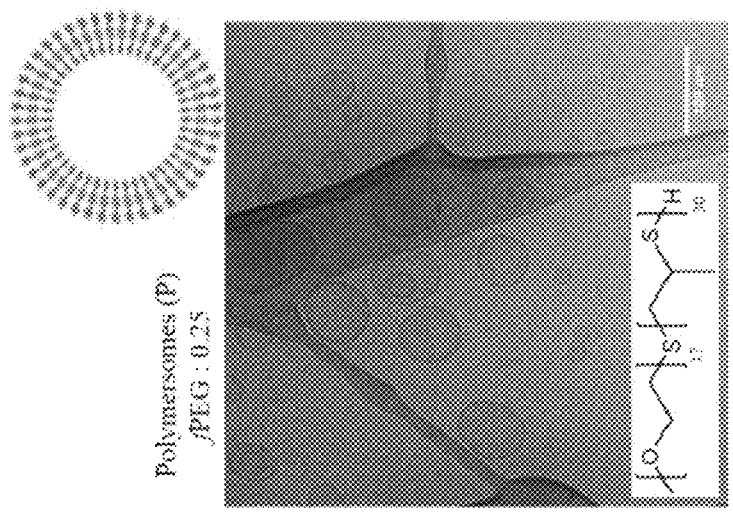
FIG. 1B Nanostructure morphologies assembled from $PEG_{17}$-bl-$PPS_{30}$ polymersomes (PS) (scale bar=100 nm) were imaged by CryoTEM. The chemical structure of each copolymer is inserted into the lower left corner of the images. The hydrophilic PEG fraction (fPEG) of the total block copolymer molecular weight and assembled nanostructure morphology are shown above each CryoTEM image.
Figure 1A:
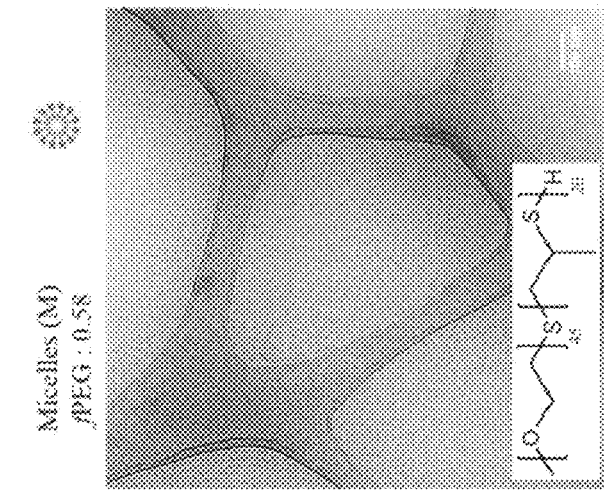
FIG. 1A Nanostructure morphologies assembled from $PEG_{45}$-bl-$PPS_{20}$ micelles (MC) (scale bar=100 nm) were imaged by CryoTEM. The chemical structure of each copolymer is inserted into the lower left corner of the images. The hydrophilic PEG fraction (fPEG) of the total block copolymer molecular weight and assembled nanostructure morphology are shown above each CryoTEM image.

To investigate the influence of nanostructure morphology on in vivo uptake by diverse cell subsets, Applicant synthesized three different nanostructures (NS), which were all self-assembled from poly(ethylene glycol)-bl-poly(propylene sulfide) (PEG-bl-PPS) block copolymers and possessed the same surface chemistry: $PEG_{45}$-bl-$PPS_{20}$ MC, $PEG_{17}$-bl-$PPS_{30}$ PS and $PEG_{44}$-bl-$PPS_{45}$ FM. FIG. 1 shows the representative size and morphology of NS as determined by cryogenic transmission electron microscopy (CryoTEM). The hydrodynamic size and size distributions of MC and PS were further characterized by DLS (Table 1).

To explore the influence of nanomaterial morphology on biodistributions at the organ level, assembled NS were loaded with real-time near infrared fluorescence (NIRF) imaging agent indocyanine green (ICG). The incorporation of ICG into nanomaterials has been demonstrated to improve its optical properties and stability [24]. Applicant characterized the stability and loading of ICG within PEG-bl-PPS MC via

TABLE 1

Physicochemical characteristics of PEG-bl-PPS nanostructure morphologies in PBS solution (pH = 7.4).

| Name of samples | Average Diameter (nm) | Polydispersity Index (PDI) | Zeta Potential (mV) |
|---|---|---|---|
| Micelles (MC) | 22.5 | 0.132 | −1.35 +/− 0.38 |
| Polymersomes (PS) | 113.7 | 0.179 | −0.20 +/− 1.68 |
| Filomicelles (FM) | N/A | N/A | −1.40 +/− 0.31 |

Abbreviations:
Micelles (MC),
Polymersomes (PS),
Filomicelles (FM).

Figure 2A:
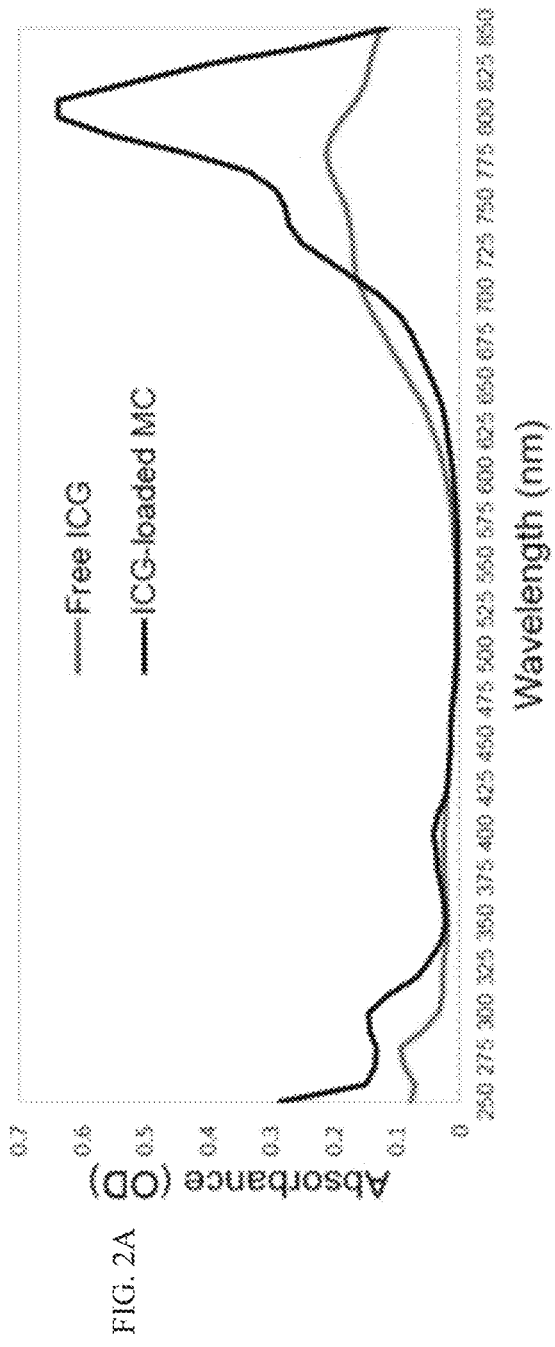
FIG. 2A Assessment of organ-level biodistributions of PEG-bl-PPS nanostructures. An IVIS optical imaging system was used to investigate the biodistributions of NIRF imaging agent indocyanine green (ICG)-loaded nanostructures in C57BL/6 mice. Absorbance spectrum of free ICG and ICG-loaded PEG-bl-PPS micelles at an excitation wavelength of 780 nm. ICG emission increased and redshifts upon loading.
Figure 2B:
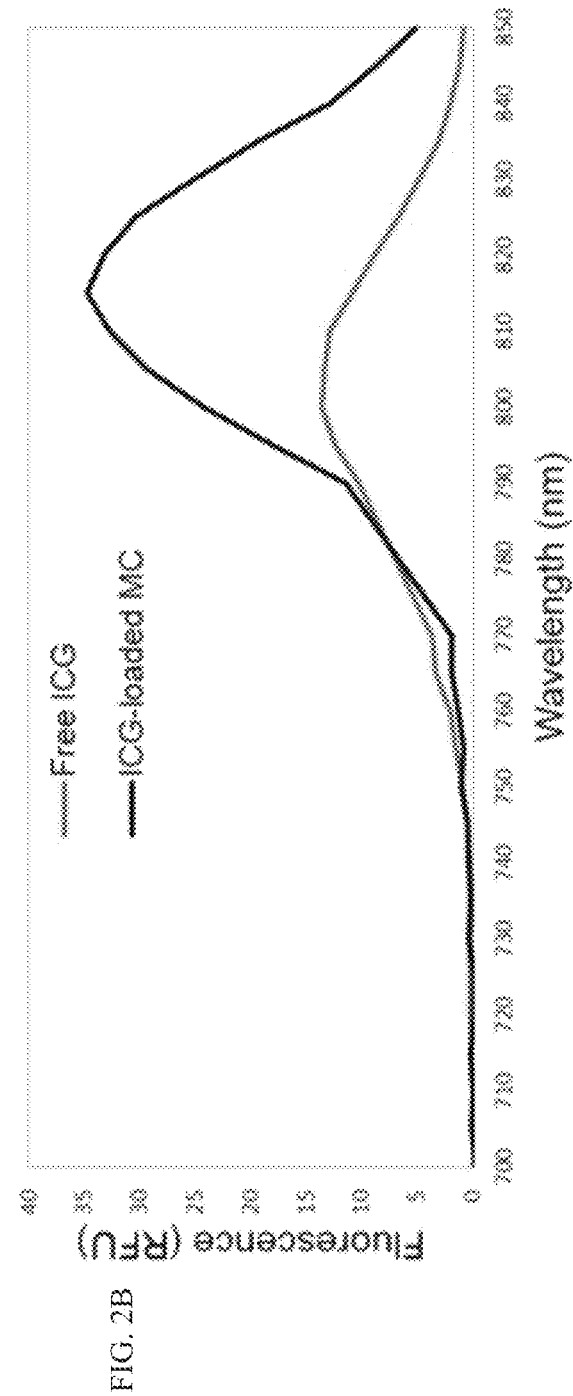
FIG. 2B Fluorescence spectrum of free ICG and ICG-loaded PEG-bl-PPS micelles at an excitation wavelength of 780 nm. ICG emission increased and redshifts upon loading.
Figure 2C:
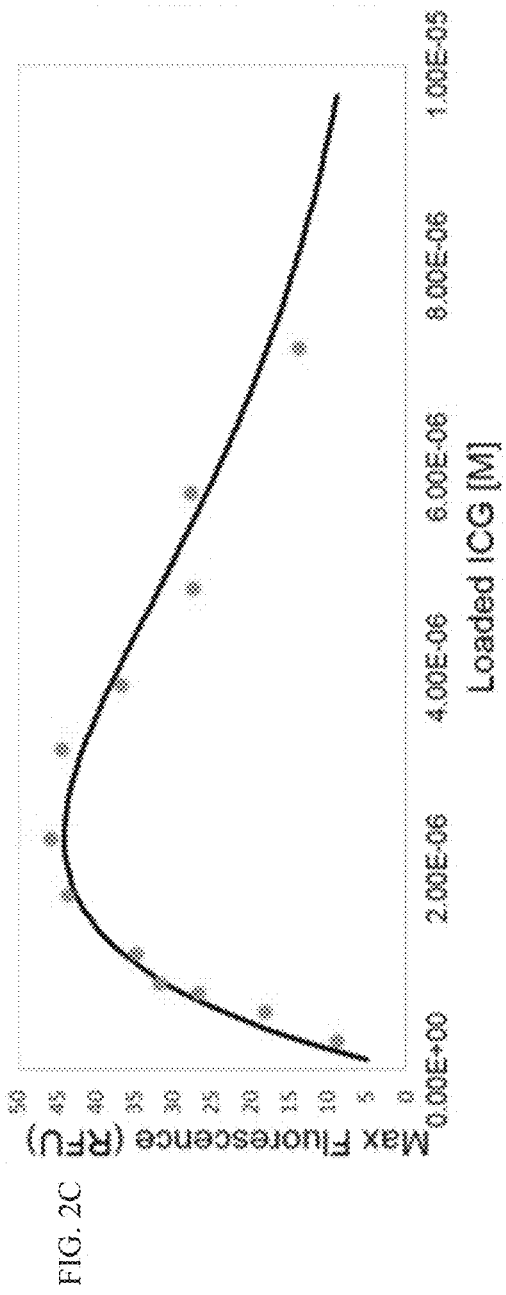
FIG. 2C The fluorescence intensity of ICG-loaded micelles at an excitation of 780 nm and emission of 810 nm at different ICG loading concentrations.
Figure 2D:
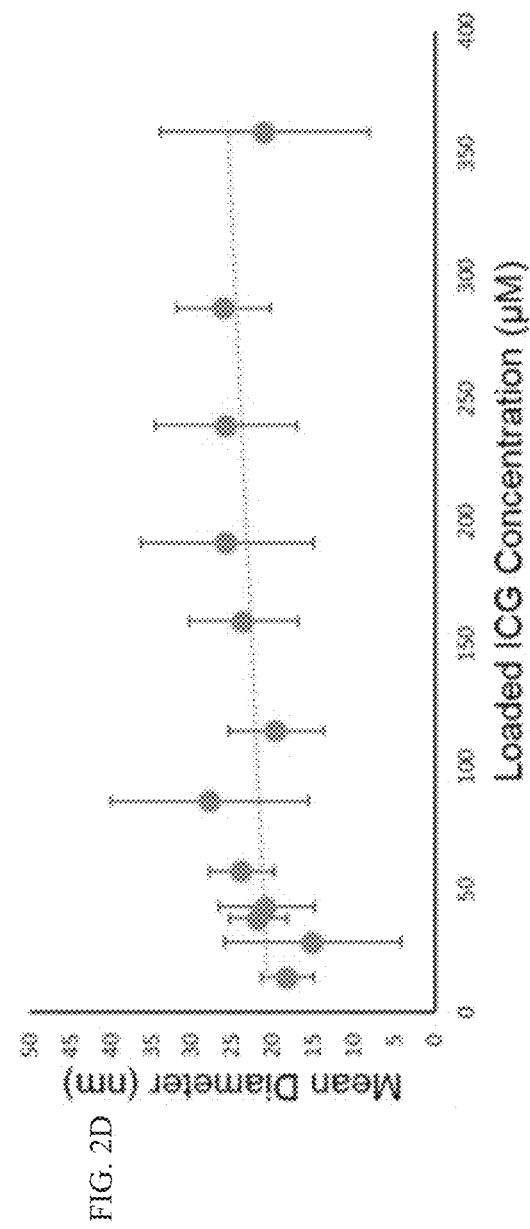
FIG. 2D Dynamic Light Scattering (DLS) measurements verified that mean diameter of micelles was not influenced by the concentration of loaded ICG.
Figure 8A:
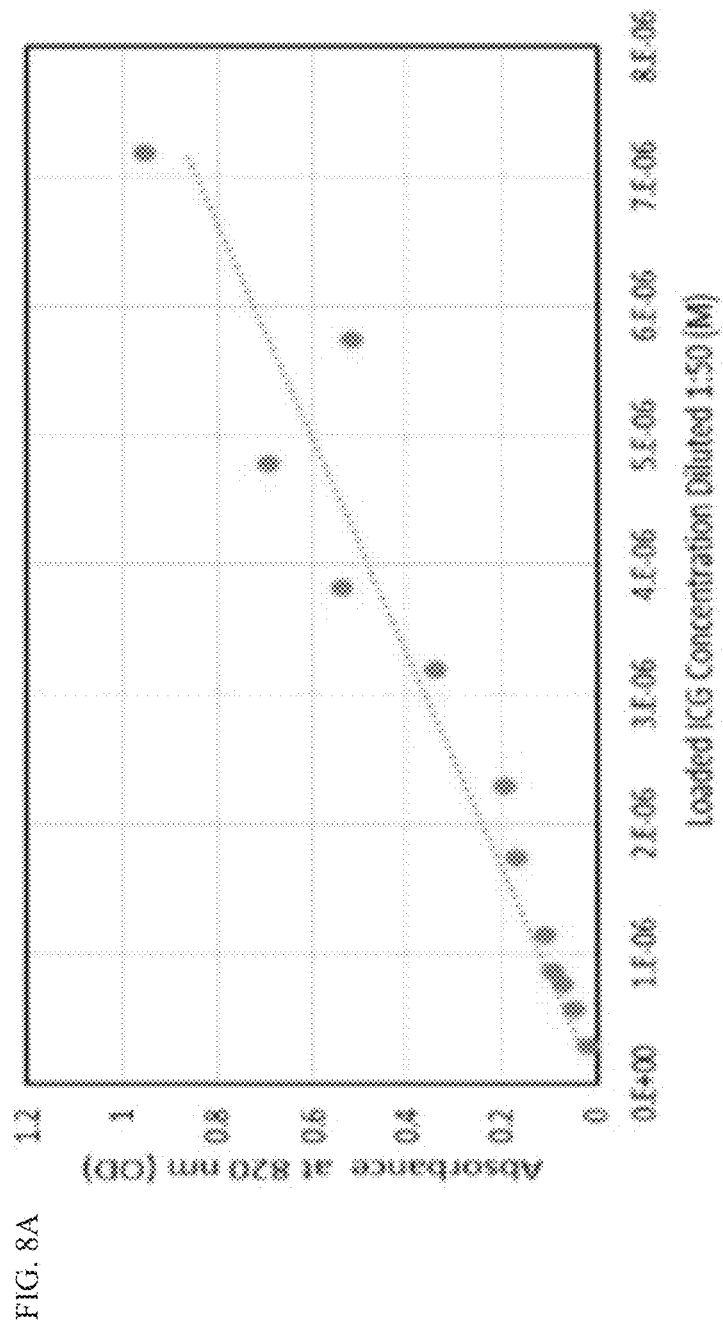
FIG. 8A Influence of ICG concentration on absorbance of PEG-bl-PPS aggregates at 820 nm, determined by UV-vis spectrometer.
Figure 8B:
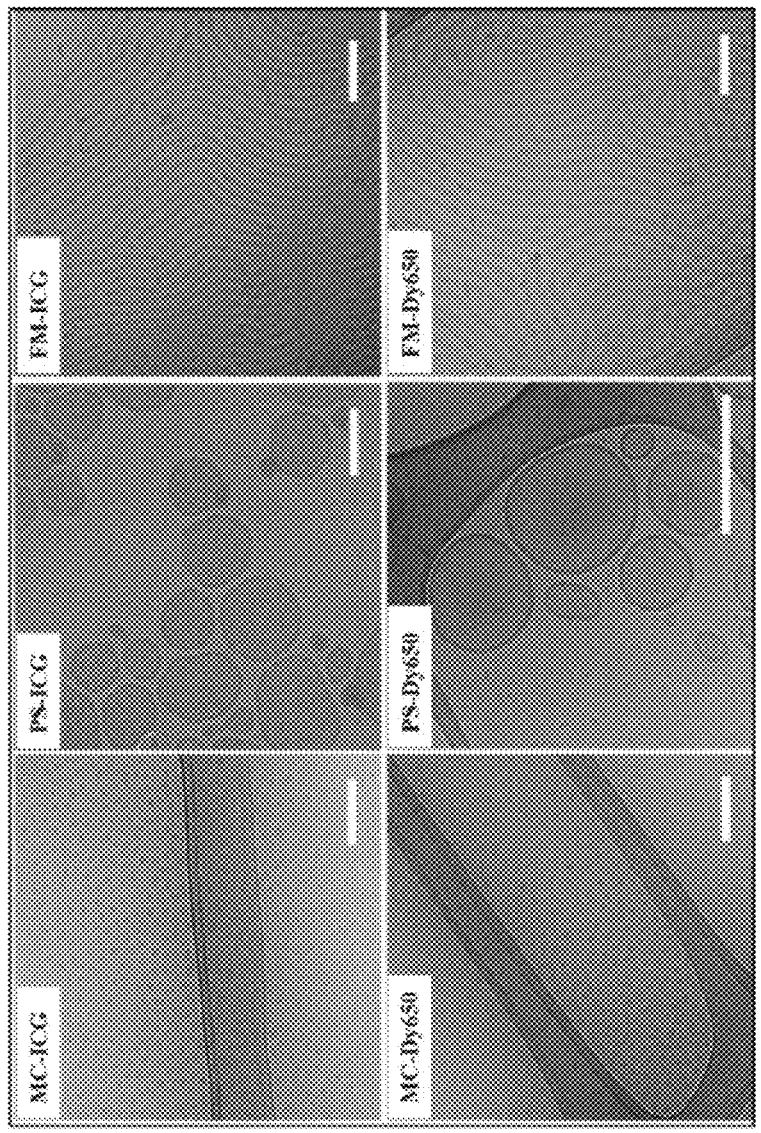
FIG. 8B CryoTEM images of ICG-loaded PEG-bl-PPS nanomaterials: ICG-loaded micelles (MC-ICG), ICG-loaded polymersomes (PS-ICG), and ICG-loaded filomicelles (FM-ICG), and Dylight 650-labeled PEG-bl-PPS nanomaterials: Dylight 650-labeled micelles (MC-Dy650), Dylight 650-labeled polymersomes (PS-Dy650), and Dylight650-labelled filomicelles (FM-dy650).
Figure 8C:
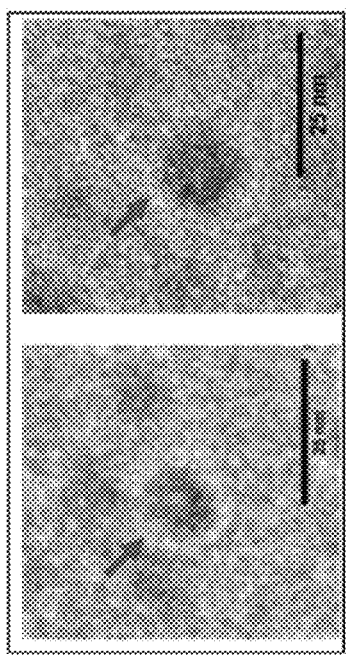
FIG. 8C CryoTEM in high magnification revealed no detectable difference in size between PEG-bl-PPS micelles with (i) or without (ii) loaded ICG.

CryoTEM, UV/vis absorbance, and fluorescence spectroscopy. ICG encapsulation efficiencies of 80%-90% were achieved for all three NS using thin film hydration, which is a robust method of loading and assembling PEG-bl-PPS NS [8, 25, 26]. The emission spectrum shifted in wavelength and increased in intensity for the same concentration of ICG when comparing ICG-loaded NS to free ICG (FIG. 2A, B). The absorbance steadily increased as the loaded ICG concentration increased within the NS (FIG. 8A). Applicant calculated the optimal loading for the strongest IR signal to be 2.3 μM, or a 33:1 molar ratio of copolymer:dye (FIG. 2 C). Self-quenching of the IR emission was observed at higher concentrations and likely due to j-aggregate induced static quenching [27]. CryoTEM images revealed no changes in size or morphology after incorporation of ICG into any of the NS (FIGS. 2D & 8 B, C).

A Distinct Organ Biodistribution was Observed for Each Nanostructure Morphology

Figure 2E:
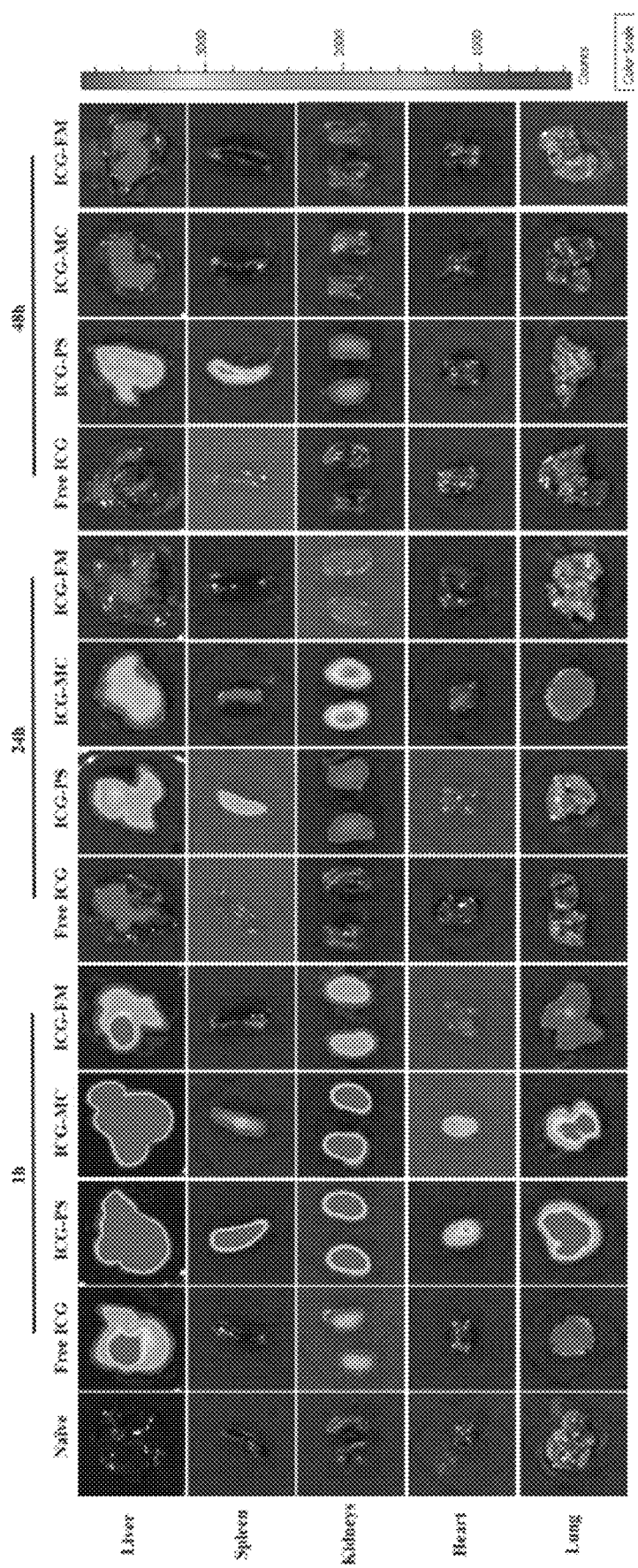
FIG. 2E Fluorescent images were obtained for representative organs (liver, spleen, kidneys, heart, and lung) 1 h, 24 h and 48 h after I.V. injection of MC, PS, and FM. N=3-6.
Figure 9A:
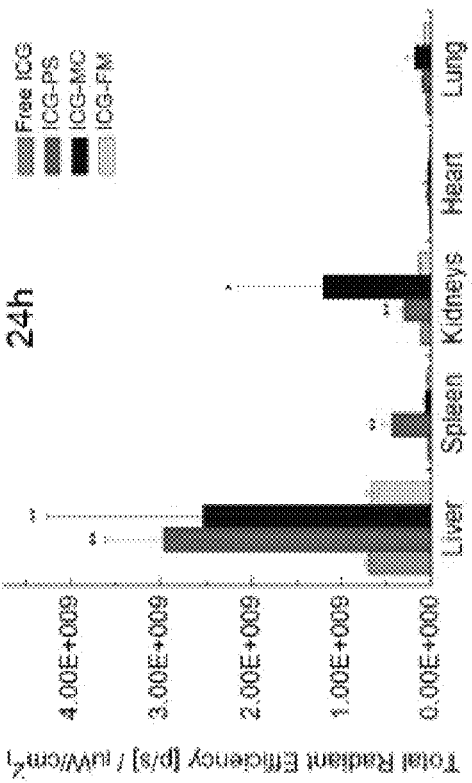
FIG. 9A Quantification of nanomaterial biodistribution in various tissues. The total radiant efficiency of ICG fluorescence in organs at 1 h was measured by Living Image 3.1 software. Data were presented as mean±SD. N=3-6. Statistical significance: *$p \leq 0.01$, $p \leq 0.005$, *$p \leq 0.0001$.
Figure 9B:
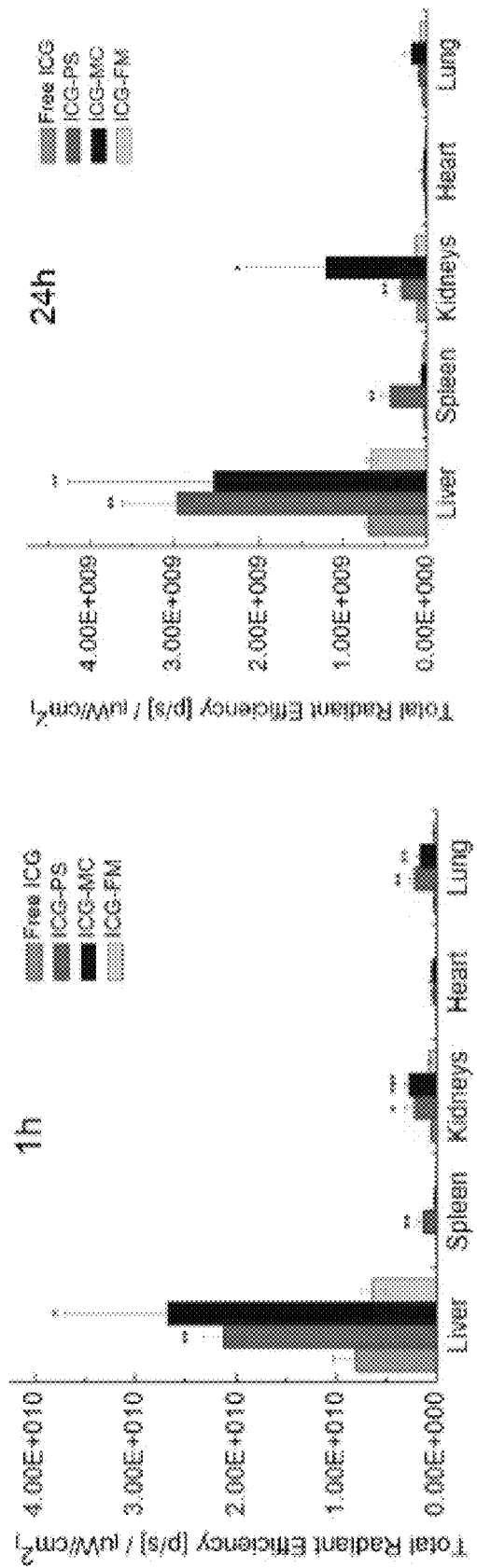
FIG. 9B Quantification of nanomaterial biodistribution in various tissues. The total radiant efficiency of ICG fluorescence in organs at the time points of 24 h was measured by Living Image 3.1 software. Data were presented as mean±SD. N=3-6. Statistical significance: *$p \leq 0.01$, $p \leq 0.005$, *$p \leq 0.0001$.
Figure 9C:
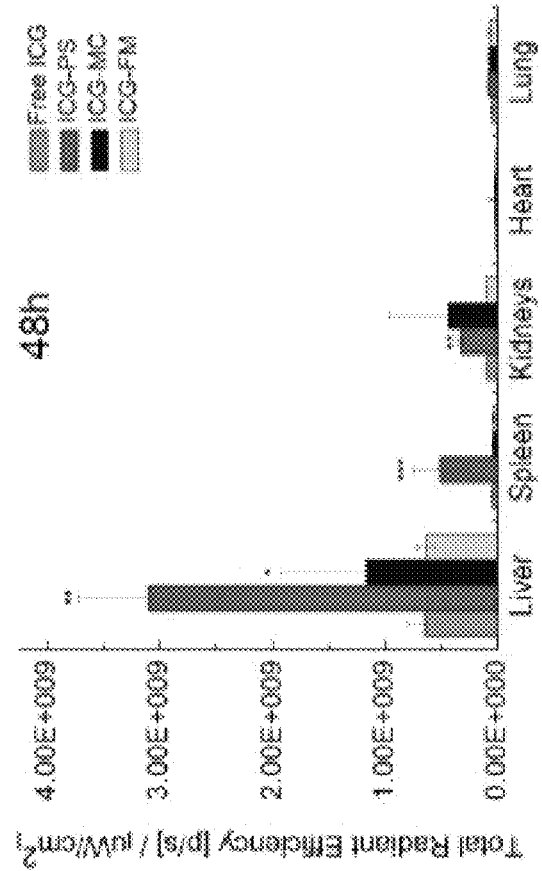
FIG. 9C Quantification of nanomaterial biodistribution in various tissues. The total radiant efficiency of ICG fluorescence in organs at 48 h was measured by Living Image 3.1 software. Data were presented as mean±SD. N=3-6. Statistical significance: *$p \leq 0.01$, $p \leq 0.005$, *$p \leq 0.0001$.

Nanomaterials have been widely used to deliver therapeutic agents in vivo, and their tissue distribution can either limit or enhance such applications. ICG-loaded MC, PS and FM were therefore assembled at a 33:1 molar ratio of copolymer:dye, and their biodistributions were compared to control injections of free form ICG and PBS in naïve C57BL/6 mice. Liver, spleen, kidneys, lung and heart were harvested and investigated with an IVIS optical imaging system. Following I.V. injection, ICG usually has a half-life of less than 10 minutes primarily due to removal from circulation in the liver [28]. As expected, Applicant observed immediate accumulation of ICG in the liver after 1 h and no observable fluorescence at the 24 h time point (FIG. 2E). In contrast, mice injected with ICG-loaded NS revealed strong fluorescent signals from multiple organs at 1 h, 24 h and 48 h post-injection, indicating a significant extension of the circulation time of ICG due to encapsulation within NS (FIG. 2E). At all time-points, stronger fluorescence from liver, spleen, and kidneys of mice treated with PS and MC was detected relative to mice treated with FM, which revealed minimal accumulation in organs at the 24 h time point (FIG. 2E). Furthermore, significantly more PS were distributed in spleen than MC, FM and free ICG ($p<0.01$) 1 h and 24 h post injection (FIG. 9A, B). Surprisingly, only PS were detectable in the spleen 48 h after injection ($p<0.001$) (FIG. 2E, FIG. 9). As the largest lymphatic organ and home to diverse immune cell populations, the spleen has been regarded as a promising target for vaccination and immunotherapy, and these results suggest PS to be an excellent nanocarrier for these applications.

The minimal detection of FM in all organs after the 1 h time-point suggested decreased uptake of FM by the MPS relative to MC and PS. This observation is consistent with previous studies comparing filamentous to spherical morphologies [7, 29, 30]. Since NS are all formed from PEG-bl-PPS copolymers of identical surface chemistry, these results further support that morphology alone can dramatically affect the biodistribution of nanomaterials in vivo. In summary, PS preferentially targeted spleen for over 48 h, while spherical MC had higher accumulation in liver and kidneys up to 24 h post injection, and FM had negligible presence within MPS cells after 1 h.

A Distinct Biodistribution was Observed within Inflammatory Cell Populations for Each Nanostructure Morphology To understand and predict the effects of delivered therapeutics, it is essential to investigate not just the general organs that are targeted, but also the specific cell populations [22, 23]. Inflammatory responses and many drug-induced side effects are generated by cells within both the MPS and broader immune system. Therefore, Applicant further investigated the influence of nanostructure morphology on the cellular distribution within organs of the MPS and immune system following I.V. administration. In order to both track and quantify the biodistributions of each NS without modifying their PEG surface chemistry or self-assembly, Applicant covalently conjugated the lipophilic fluorophore DyLight 650 maleimide onto the thiol-functionalized ends of the hydrophobic PPS blocks of the PEG-bl-PPS copolymers after their assembly in aqueous solution. The DyLight 650-labeled NS were verified to be stable and unchanged in size and morphology by CryoTEM (FIG. 8A).

Figure 3J:
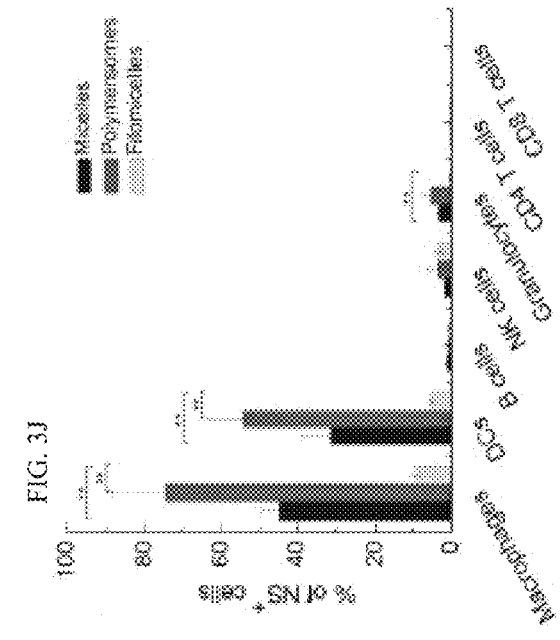
FIG. 3J Flow cytometric analysis of the association of MC, PS and FM with immune cells isolated from lymph nodes of C57BL/6 mice after time points of 48 h following tail vein injection. Histograms show the average percentages±standard deviation (SD) of each indicated cell type that was nanostructure positive (NS+). Cells same as in FIG. 3A. N=3 in each group, two independent experiments. Statistical significance: *p≤0.01, p≤0.005, *p≤0.0001.
Figure 3L:
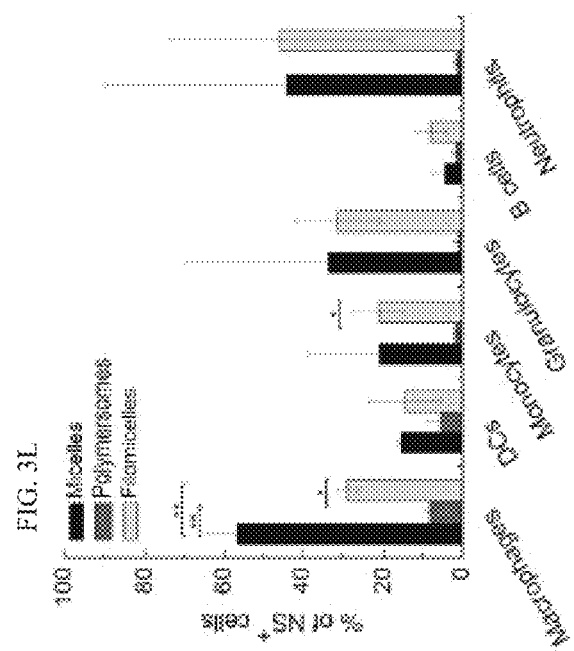
FIG. 3L Flow cytometric analysis of the association of MC, PS and FM with immune cells isolated from blood of C57BL/6 mice after time points of 48 h following tail vein injection. Histograms show the average percentages±standard deviation (SD) of each indicated cell type that was nanostructure positive (NS+). Cells same as in FIG. 3A. N=3 in each group, two independent experiments. Statistical significance: *p≤0.01, p≤0.005, *p≤0.0001.
Figure 3I:
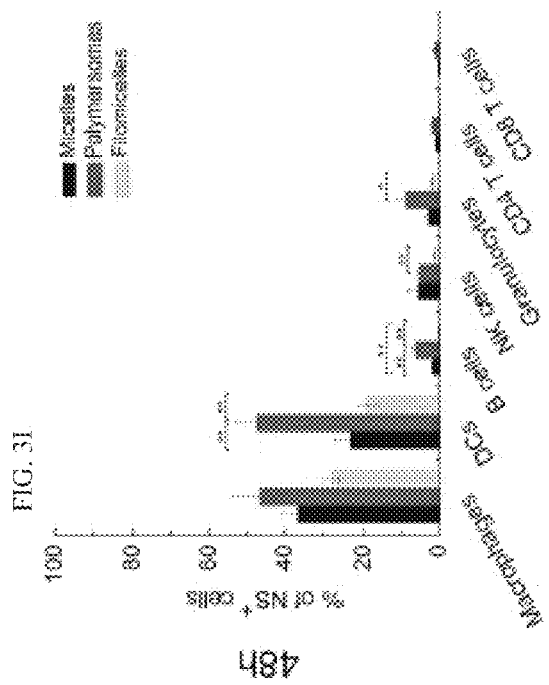
FIG. 3I Flow cytometric analysis of the association of MC, PS and FM with immune cells isolated from spleen of C57BL/6 mice after time points of 48 h following tail vein injection. Histograms show the average percentages±standard deviation (SD) of each indicated cell type that was nanostructure positive (NS+). Cells same as in FIG. 3A. N=3 in each group, two independent experiments. Statistical significance: *$p≤0.01$, $p≤0.005$, *$p≤0.0001$.
Figure 11:
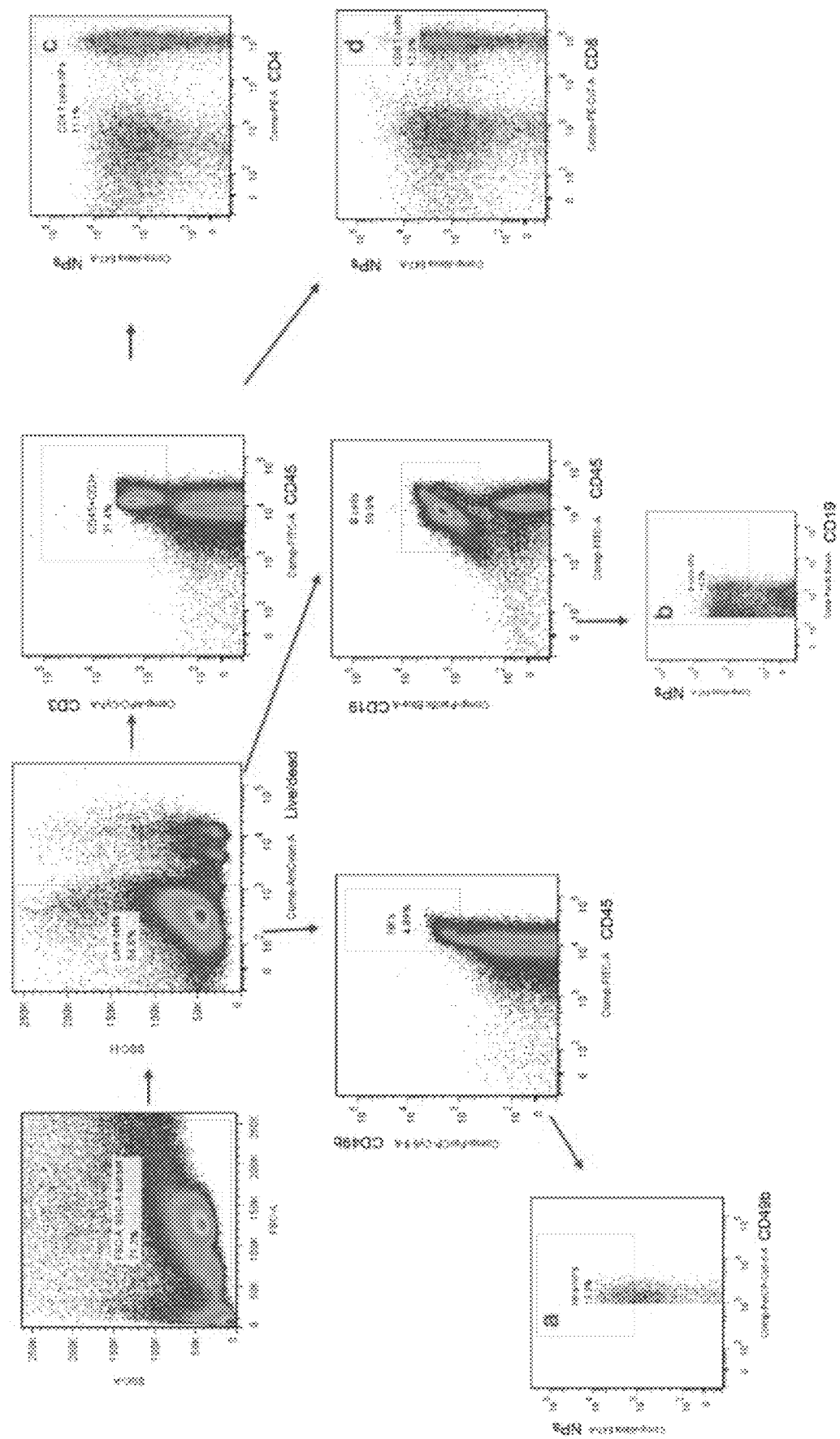
FIG. 11 Flow cytometry gating strategy for the analysis of immune cells. Sample cells were obtained from a mouse spleen injected with Dylight 650 labeled-nanomaterials. Immune cells described in the manuscript are determined as below:
I. (a) natural killer cells: CD45$^+$CD49b$^+$; (b) B cells: CD45$^+$CD19$^+$; (c) CD4 T cells: CD45$^+$CD3$^+$CD4$^+$; (d) CD8 T cells: CD45$^+$CD3$^+$CD8$^+$.
II. (a) dendritic cells (DCs): CD11c$^+$; (b) granulocytes: Gr-1$^+$CD11b$^+$; (c) PreDCs: I-A/I-E-CD11c$^+$; (d) mature DCs: I-A/I-E$^+$CD11c$^+$; (e) plasmacytoid DCs: I-A/I-E$^+$CD11c$^+$Gr-1$^+$B220$^+$; (f) CD8$^+$DCs: I-A/I-E$^+$CD11c$^+$CD8$^+$; (g) CD11b$^+$DCs: I-A/I-E$^+$CD11c$^+$CD11b$^+$.
III. (a) macrophages: CD11b$^+$F4/80$^+$; (b) neutrophils: CD11b$^+$Ly6G$^+$; (c) Monocytes: CD11b$^+$CD11c–Ly6G–SS-Clow; (d) Ly6C– monocytes: CD11b$^+$CD11c–Ly6C–; (e) Ly6C$^+$ monocytes: CD11b$^+$CD11c–Ly6C$^+$.
Figure 11:
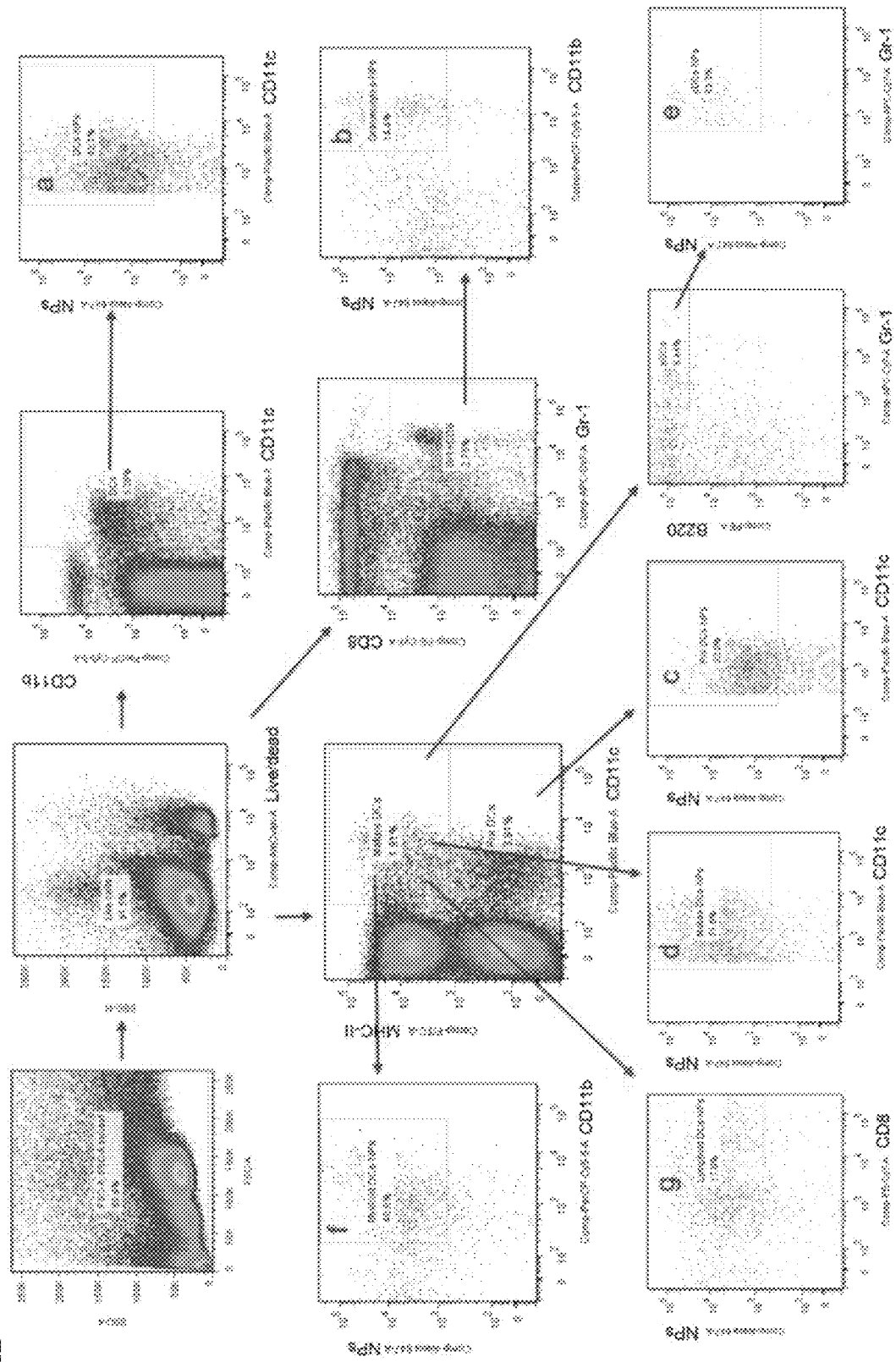
Figure 11:
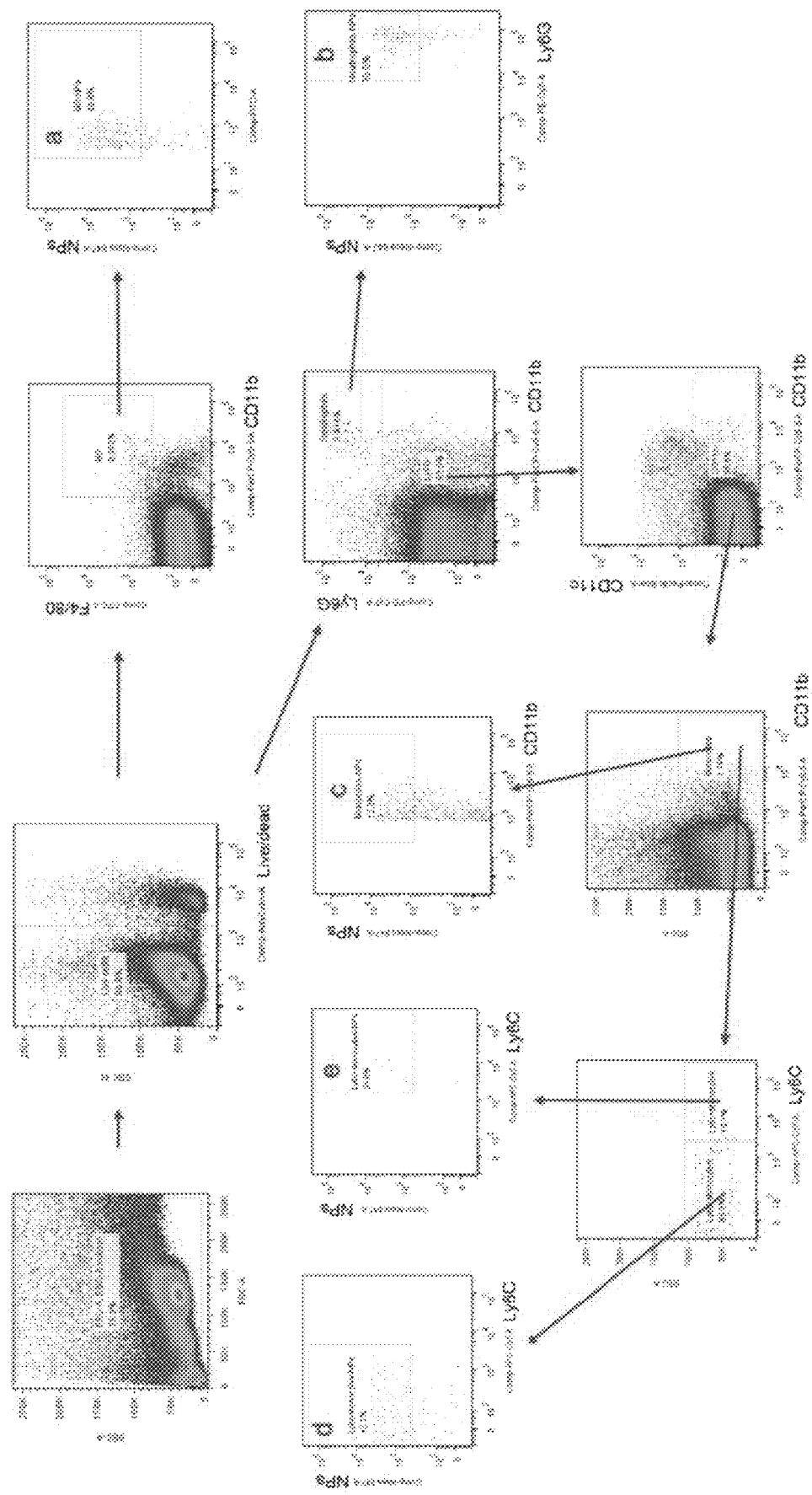
Figures 12A, 12B, 12C:
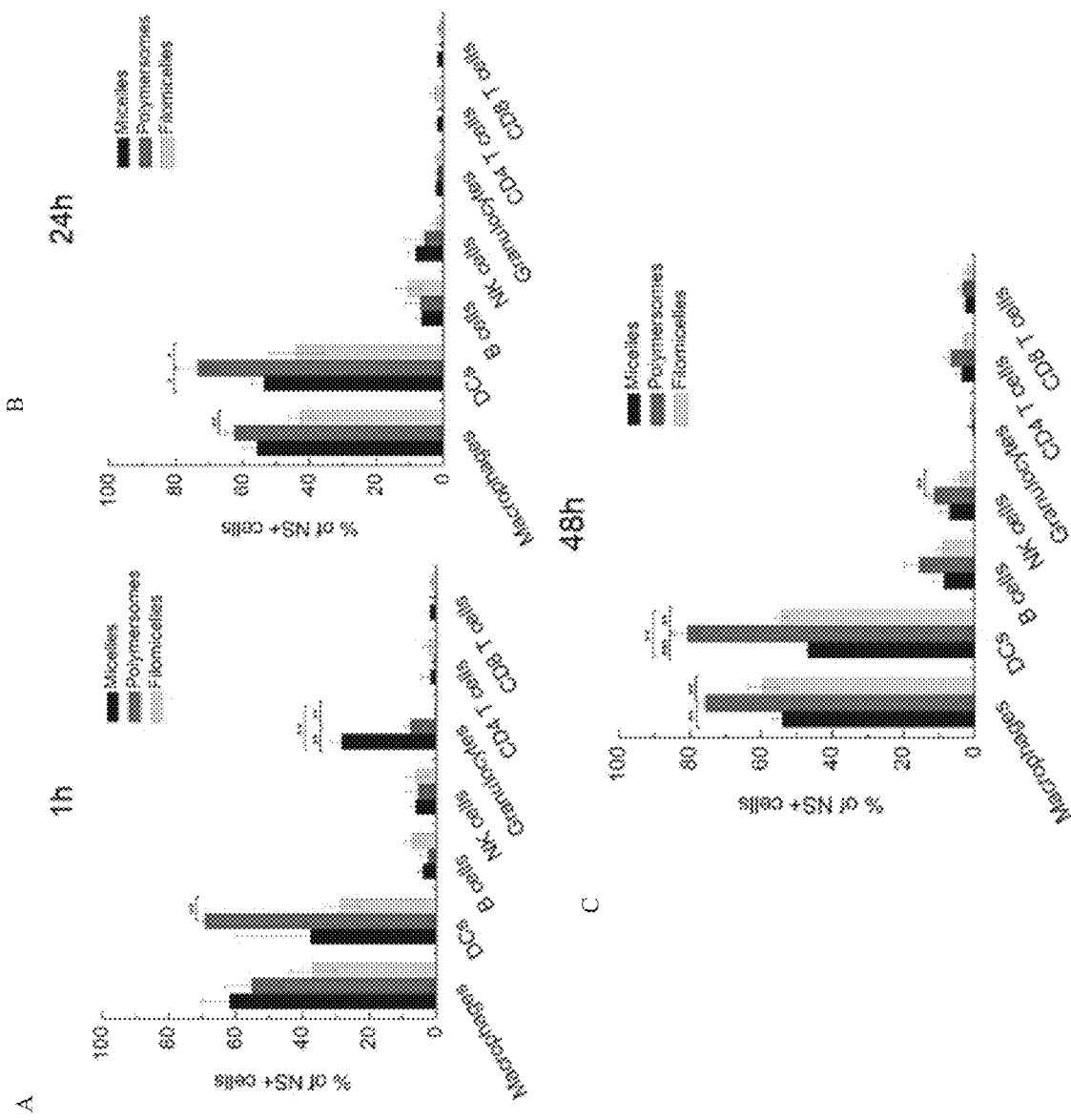
FIGS. 12A-12C Nanostructure morphology altered the distribution of PEG-bl-PPS nanomaterials in immune cells of naïve mice. Biodistribution of MC, PS and FM in various immune cells from kidneys of C57BL/6 mice 1 h (A), 24 h (B), and 48 h (C) after I.V. injections. Data were analyzed by flow cytometry and flowJo software (FLOWJO, LLC, Ashland Oreg.). Macrophages: CD11b$^+$F4/80$^+$; dendritic cells: CD11c$^+$; B cells: CD45$^+$CD19$^+$; natural killer cells: CD45$^+$CD49b$^+$; granulocytes: Gr-1$^+$CD11b$^+$; CD4 T cells: CD45$^+$CD3$^+$CD4$^+$; CD8 T cells: CD45$^+$CD3$^+$CD8$^+$. Gating strategies are shown in FIG. 11. N=3 in each group, two independent experiments. Statistical significance: *$p \leq 0.01$, $p \leq 0.005$, *$p \leq 0.0001$.

Multi-color flow cytometry was performed to evaluate the uptake of NS of the present invention within cells of the innate and adaptive immune system. Mice were administered DyLight 650-labeled PS, MC and FM by tail vein injection. After different time points (1 h, 24 h, and 48 h), spleen, LN, liver, kidneys, and blood were collected and prepared into single cell suspensions for analysis (gating strategies shown in FIG. 11). For all organs evaluated, NS were predominantly taken up by phagocytic cells in the MPS (FIG. 3, FIG. 12). In accordance with the organ-level ICG analysis, significantly higher PS association was observed for immune cells in the spleen, where all NS associated strongly with macrophages and DC and minimally with NK cells, granulocytes and T cells (FIG. 3A, E, I). Among these, between 30%-40% of isolated macrophages and DC were PS positive (PS$^+$) at the 1 h time point, which were significantly higher than for MC ($p<0.0001$) and FM ($p<0.005$) (FIG. 3A). Although no significant differences were observed between PS uptake and MC uptake for macrophages, significantly higher percentages of DC were PS$^+$ 24 h ($p<0.01$) and 48 h ($p<0.005$) post injections (FIG. 3E, I). For MC and FM, the cellular distribution showed no significant difference after 24 h (FIG. 3E, I).

I.V.-injected nanomaterials require more time to reach LNs, since they must first exit circulation and drain from peripheral tissue. As expected, uptake of NS by immune cells in LNs was delayed relative to the spleen and liver, and minimal association with cells was detected until 24 h-48 h post injection (FIG. 3B, F, J). Significantly more PS$^+$ macrophages and PS$^+$ DC were found relative to MC$^+$ macrophages ($p<0.005$), MC+ DC ($p<0.005$), FM$^+$ macrophages ($p<0.01$) and FM$^+$ DC ($p<0.005$) 24 h and 48 h after administration (FIG. 3F, J).

Figure 3K:
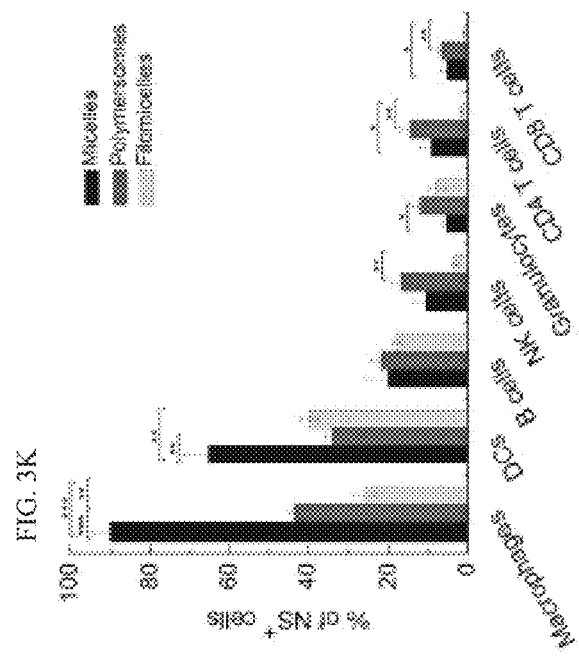
FIG. 3K Flow cytometric analysis of the association of MC, PS and FM with immune cells isolated from liver of C57BL/6 mice after time points of 48 h following tail vein injection. Histograms show the average percentages±standard deviation (SD) of each indicated cell type that was nanostructure positive (NS+). Cells same as in FIG. 3A. N=3 in each group, two independent experiments. Statistical significance: *p≤0.01, p≤0.005, *p≤0.0001.

As the main blood-filtering organ, the liver is enriched in macrophages, DC, NK cells, and T cells, but contains minimal granulocytes [31]. All NS were detected at high levels in liver macrophages (FIG. 3C, G, K). At 1 h and 24 h post-injection, PS$^+$ and MC$^+$ macrophages and DC showed no significant difference in uptake (FIGS. 3C and G). However, after 48 h administration, MC was found to target over 90% of macrophages and 65% of DC in the liver, which is significantly more than PS (targeting 40% of macrophages, $p<0.0001$ and 35% of DC, $p<0.005$) and FM (targeting 25% of macrophages, $p<0.0001$ and 40% of DC, $p<0.005$) (FIG. 3K).

Figure 10:
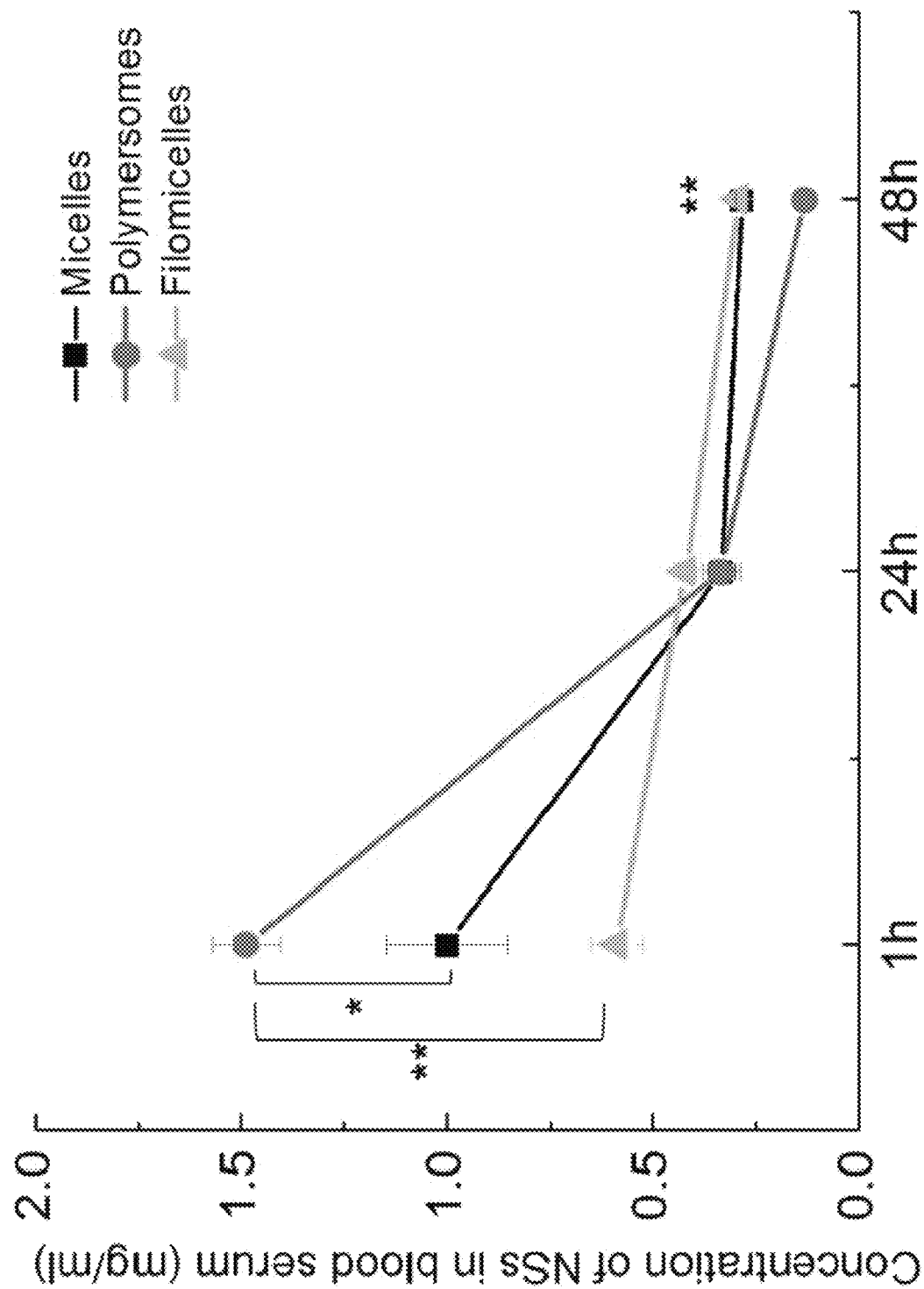
FIG. 10 Determination of nanomaterial circulation in blood. Concentration of MC, PS and FM) in blood serum was measured with a fluorescence spectrometer (EX/EM=652/672 nm) after different time points (1 h, 24 h and 48 h) after I.V. injection in C57BL/6 mice. Data represent mean±SD, N=3, two independent experiments. Statistical significance: *$p \leq 0.01$, $p \leq 0.005$, *$p \leq 0.0001$.

FM exhibited low association with immune cells in the MPS, but, surprisingly, were taken up by significantly higher percentages of monocytes, granulocytes (predominantly neutrophils), and macrophages in blood relative to PS and MC (FIG. 3D, H, L). FM associated with approximately 90% of blood neutrophils 1 h after I.V. administration and up to 80% of blood monocytes after 24 h (FIG. 3D, E). This rapid uptake by blood cells may have contributed to the significantly lower serum concentration of FM at the 1 h time point relative to MC and PS ($p<0.005$) (FIG. 10). The relatively steady FM blood concentration over the course of 48 h is possibly due to minimal association with MPS cells in the liver, spleen and LN, allowing longer blood circulation and increased opportunity for uptake by blood phagocytes.

In summary, PS exhibited superior targeting of DC in lymphoid organs (spleen and LN), while MC showed preferential uptake by macrophages in the liver. FM were rapidly taken up by blood-resident monocytes and neutrophils, and exhibited long circulation time and decreased uptake by MPS cells in the liver, spleen, and LN. These results highlight the promising potential of NSET for detection and modulation of distinct inflammatory cell populations, and in particular for the targeting of DC by the PS morphology.

Polymersomes Target Relevant DC Subsets in Lymphoid Organs of Naïve Mice

Although of critical importance for understanding and predicting inflammatory responses, very little research has been performed to explore the cellular biodistribution of nanomaterials within DC subsets. Applicant therefore used flow cytometry to probe the influence of morphology on the in vivo uptake of NS by several key DC populations. Multiple subsets of DC, which possess different cell surface markers, cytokine expression and immunological functions, have been identified [32]. DC can be broadly divided into classical DC (cDC) and plasmacytoid DC (pDC) [33]. Murine cDC are further divided into myeloid DC (CD11b$^+$ DC) and lymphoid (CD8$^+$ DC), which are respectively analogous to human CD1c$^+$/cDC2 that have diverse Th1, Th2 or Th17 polarized antigen/adjuvant-dependent responses and CD141$^+$/cDC1 cells that efficiently cross-present antigen for cytotoxic T cell activation [1, 32, 34]. pDCs both active atheroprotective regulatory T cells (Tregs) in an indoleamine-pyrrole 2,3-dioxygenase (IDO)-dependent manner as well as release proatherogenic type I interferons (IFN) [35, 36]. Thus it is critical to understand which specific subsets of DC are targeted by nanomaterials when developing strategies for therapy and diagnosis.

Interestingly, PS demonstrated significantly higher association with all DC subsets than MC and FM (FIG. 4), which is consistent with the Applicant's previous data showing more PS$^+$ DC than MC$^+$ and FM$^+$ DC in the spleen and draining LNs (FIG. 3). Furthermore, unlike MC and FM, PS associated with mature DC to a significantly higher degree than preDC at all time points in the spleen and 24 h post injection in the LN. Although this may suggest that uptake of PS induced DC maturation, PEG-bl-PPS NS are non-immunogenic and non-inflammatory unless loaded with antigen or adjuvant [25, 26]. An alternative explanation is that the preferred mechanism for uptake of PS was receptor mediated endocytosis or phagocytosis while MC and FM entered cells primarily via macropinocytosis, since macropinocytosis is dramatically reduced following DC maturation [37]. Receptor-mediated endocytosis is known to be dependent on nanomaterial shape and size and has been modeled as a function of cell surface receptor surface density and membrane diffusion [4].

Figures 5A, 5B, 5C, 5D:
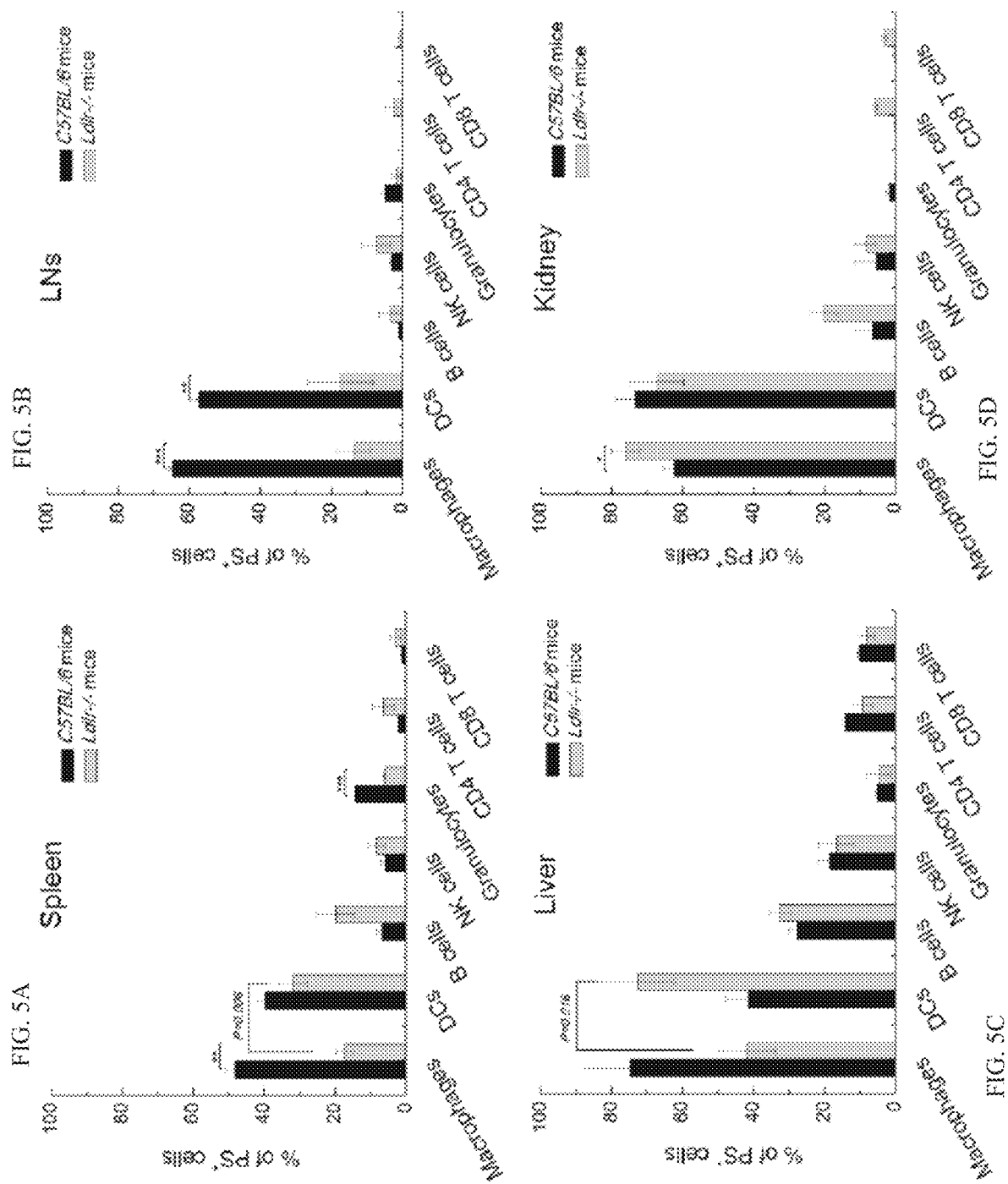
FIG. 5A Flow cytometric analysis of Dylight 650-labeled PS uptake by various immune cell populations of spleen 24 h after I.V. injection in naïve C57BL/6 mice and atherosclerotic (Ldlr$^{-/-}$) mice on a C57Bl/6 background. Histograms show the average percentages±standard deviation (SD) of each indicated cell type that was PS positive (PS+). Definitions which apply to FIGS. 5A-F: Macrophages: CD11b$^+$F4/80$^+$; DC: CD11c$^+$; B cells: CD45$^+$CD19$^+$; NK cells: CD45$^+$CD49b$^+$; granulocytes: Gr-1$^+$CD11b$^+$; CD4 T cells: CD45$^+$CD3$^+$CD4$^+$; CD8 T cells: CD45$^+$CD3$^+$CD8$^+$. N=3 for each group, two independent experiments. Statistical significance: *p≤0.01, p≤0.005, *p≤0.0001.
FIG. 5B Flow cytometric analysis of Dylight 650-labeled PS uptake by various immune cell populations of LNs (B) 24 h after I.V. injection in naïve C57BL/6 mice and atherosclerotic (Ldlr$^{-/-}$) mice on a C57Bl/6 background. Histograms show the average percentages±standard deviation (SD) of each indicated cell type that was PS positive (PS+). N=3 for each group, two independent experiments. Statistical significance: *p≤0.01, p≤0.005, *p≤0.0001.
FIG. 5C Flow cytometric analysis of Dylight 650-labeled PS uptake by various immune cell populations of liver 24 h after I.V. injection in naïve C57BL/6 mice and atherosclerotic (Ldlr$^{-/-}$) mice on a C57Bl/6 background. Histograms show the average percentages±standard deviation (SD) of each indicated cell type that was PS positive (PS+). N=3 for each group, two independent experiments. Statistical significance: *p≤0.01, p≤0.005, *p≤0.0001.
FIG. 5D Flow cytometric analysis of Dylight 650-labeled PS uptake by various immune cell populations of kidneys 24 h after I.V. injection in naïve C57BL/6 mice and atherosclerotic (Ldlr$^{-/-}$) mice on a C57Bl/6 background. Histograms show the average percentages±standard deviation (SD) of each indicated cell type that was PS positive (PS+). N=3 for each group, two independent experiments. Statistical significance: *p≤0.01, p≤0.005, *p≤0.0001.
Figure 6A:
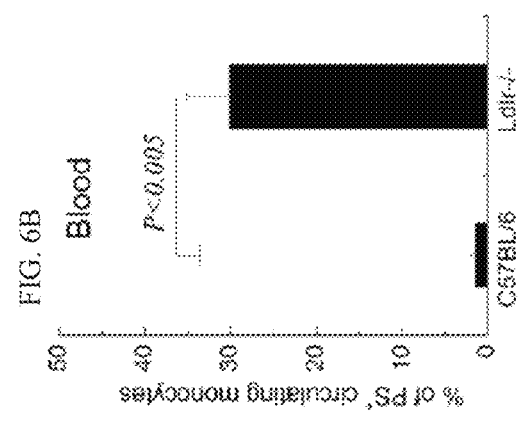
FIG. 6A Spleen 24 h after I.V. injection of Dylight 650-labeled PS were analyzed by flow cytometry. Histograms show the average percentages±standard deviation (SD) of each indicated cell type that was PS positive (PS$^+$). Definitions that apply for FIG. 6A-E: PreDC: I-A/I-E-CD11c$^+$; mature DCs: I-A/I-E$^+$CD11c$^+$; plasmacytoid DCs: I-A/I-E$^+$CD11c$^+$Gr-1$^+$B220$^+$; CD8$^+$ DCs: I-A/I-E$^+$CD11c$^+$CD8$^+$; CD11b$^+$ DCs: I-A/I-E$^+$CD11c$^+$CD11b$^+$. N=3 in each group, two independent experiments. Statistical significance: *p≤0.01, p≤0.005, *p≤0.0001.
Figure 6B:
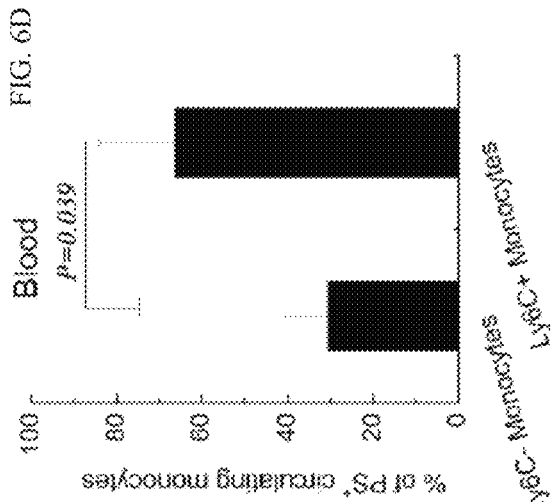
FIG. 6B Flow cytometric analysis showed significantly higher uptake of PS by circulating monocytes in Ldlr$^{-/-}$ mice than C57BL/6 mice 24 h after tail vein injection.
Figure 6C:
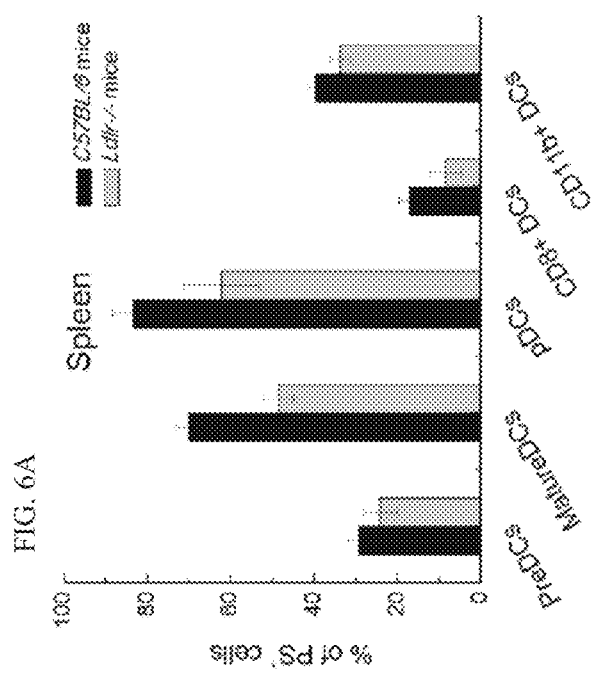
FIG. 6C LNs 24 h after I.V. injection of Dylight 650-labeled PS were analyzed by flow cytometry. Histograms show the average percentages±standard deviation (SD) of each indicated cell type that was PS positive (PS$^+$). N=3 in each group, two independent experiments. Statistical significance: *p≤0.01, p≤0.005, *p≤0.0001.

The percentage of PS$^+$ pDC was significantly higher than that of MC$^+$ and FM$^+$ pDC at all time points tested in the spleen and 24 h post injection in the LN (FIG. 4). At only 1 h after injection, over 60% of isolated pDC were PS$^+$ (FIG. 4A). Most strikingly, PS showed very high capacity to target pDC (up to 85% in spleen and 75% in LNs) compared to CD11b$^+$ DC (~40% in spleen and 45% in LNs) and CD8$^+$ DC (~20% in spleen and LNs) (FIG. 4B, E). Overall, nanostructure morphology revealed significantly different distribution in DC populations, with PS exhibiting a significantly higher capacity to target all DC subsets in lymphoid organs (spleen and LNs) with a particular affinity for pDC. In addition to their well-documented role in responding to viral infection with a massive production of type I interferon (IFN), pDCs are attracting more attention as targets in immunotherapies due to their roles in tolerance and atherosclerosis [32, 38]. PS may therefore serve as an excellent vehicle for nanomaterial-based immunotherapies, and for these reasons Applicant elected to utilize PS to target splenic and lesion-resident DC in a mouse model of atherosclerosis. Polymersomes Target Significantly Lower Percentages of Macrophages in Spleen without Effecting Uptake by Dendritic Cells in Atherosclerotic Mice Vs Naïve Mice The importance of DC in innate and adaptive immunity is widely acknowledged in numerous inflammatory diseases, including atherosclerosis. Given the attractive capacity of PS to target DC in the spleen and LNs in naïve mice, Applicant further studied the cellular distribution of PS in atherosclerotic Ldlr$^{-/-}$ mice on a C57BL/6 background [39]. To compare with naïve C57BL/6 mice, Ldlr$^{-/-}$ mice fed a high fat diet for 16 weeks were injected intravenously with the same concentration of DyLight 650-labeled PS. Previous data has indicated peak uptake of PS by DC at the 24 h post-I.V. injection time point (FIG. 4), spleen, LN, liver, kidneys, and aorta were harvested after 24 h and analyzed by flow cytometry as before (FIG. 5). The percentages of PS$^+$ macrophages were significantly lower in spleen (p<0.005) of Ldlr$_{-/-}$ mice, while uptake of PS by DC remained unchanged (FIG. 5A). As a result, uptake of PS by splenic DC was significantly higher than for macrophages (p=0.006) in atherosclerotic mice, and a similar effect was observed in the liver (p=0.016) (FIG. 5A, C). In LNs however, PS displayed a significant decrease in the association with both macrophages (p<0.0001) and DC (p<0.005) in atherosclerotic compared to non-atherosclerotic mice (FIG. 5B). To further assess PS uptake by DC in atherosclerotic mice, DC subsets in spleen and LNs were analyzed by flow cytometry (FIG. 6A, C). No significant difference of association among splenic DC subsets (FIG. 6A) was shown, but a consistent and significant decreased association was observed among all tested DC subsets in LNs (FIG. 6C).

Figure 6D:
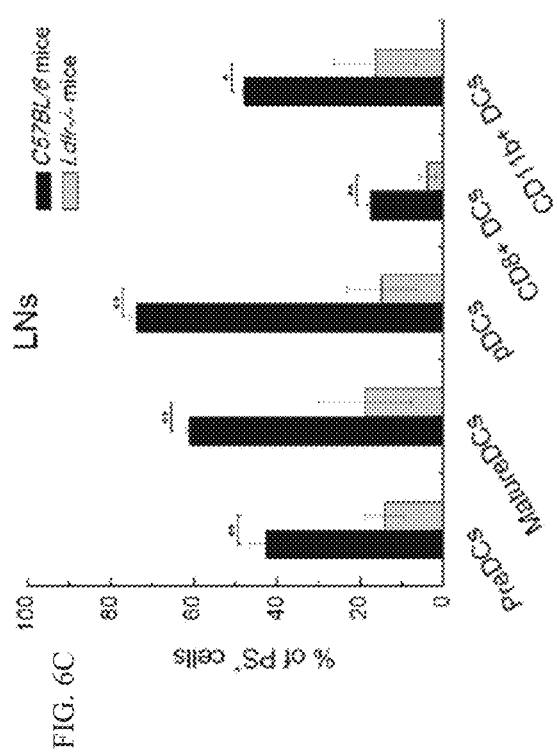
FIG. 6D Distribution of PS in circulating Ly6C$^-$ and Ly6C$^+$ monocytes in Ldlr$^{-/-}$ mice 24 h after I.V. injection. Ly6C$^-$ monocytes: CD11b$^+$CD11c$^-$Ly6C$^-$; Ly6C$^+$ monocytes: CD11b$^+$CD11c$^-$Ly6C$^+$. N=3 in each group, two independent experiments. Statistical significance: *p≤0.01, p≤0.005, *p≤0.0001.

Monocytosis is a common observance during atherosclerosis wherein the bone marrow and spleen overproduce monocytes that enter the blood circulation and contribute to hypercholesterolemia [40]. Applicant hypothesized that increased levels of circulating monocytes in blood might contribute to the decreased presence of PS$^+$ macrophages in the spleen and liver of atherosclerotic mice. To confirm this hypothesis, Applicant investigated the association of PS with circulating monocytes in blood of Ldlr$^{-/-}$ and naïve mice. In Ldlr$^{-/-}$ mice, 30% of circulating blood monocytes were PS$^+$ (p<0.005) while less than 2% were PS+ in naïve mice (FIG. 6B). In addition, PS were found to associate more with Ly6C$^+$ monocytes than Ly6C− monocytes (p=0.039) (FIG. 6D). Ly6C$^+$ monocytes are the primary source of inflammatory lipid-laden foam cells that are found in atherosclerotic lesions [41]. These data verified that blood monocytes were more efficiently removing PS from circulation in atherosclerotic mice, which combined with monocytosis may explain the decreased available PS for uptake by phagocytes in the spleen and LN. Overall, the results demonstrate significant differences in nanomaterial uptake under conditions of atherosclerosis notably in LNs. This suggests that clinical strategies involving nanomaterials, particularly for vaccination and immunotherapy that require targeting of LN-resident cell populations, may have different efficacy under conditions of atherosclerosis, which has been shown to impair lymphatic fluid transport [42].

Polymersomes Target Resident Dendritic Cells in Lesions of Atherosclerotic Mice

The pool of circulating DC has been shown to decrease as DC numbers increase in vulnerable inflamed vascular tissue of atherosclerotic mice and humans [43]. These DC contribute to atherosclerotic inflammation by activating T cells that weaken the plaque boundary and by releasing chemokines and cytokines to respectively attract and activate additional inflammatory cells. While the targeting of monocytes and macrophages with nanomaterial has been extensively investigated for the treatment of heart disease, atheroma-resident DC present an untapped and under investigated target for both detecting vulnerable plaques and treating the local inflammation [11]. Applicant therefore investigated the targeting ability of PS to DC in the aorta, which is recognized as a primary location for vascular lesions in Ldlr$^{-/-}$ mice. Over 25% of DC were observed to be PS$^+$ in the aorta of atherosclerotic mice, which was significantly higher than for macrophages, monocytes and all other isolated immune cell populations (p<0.005) (FIG. 7A). All DC subsets investigated in the lesions were targeted equally (between 15-30%

Figure 13:
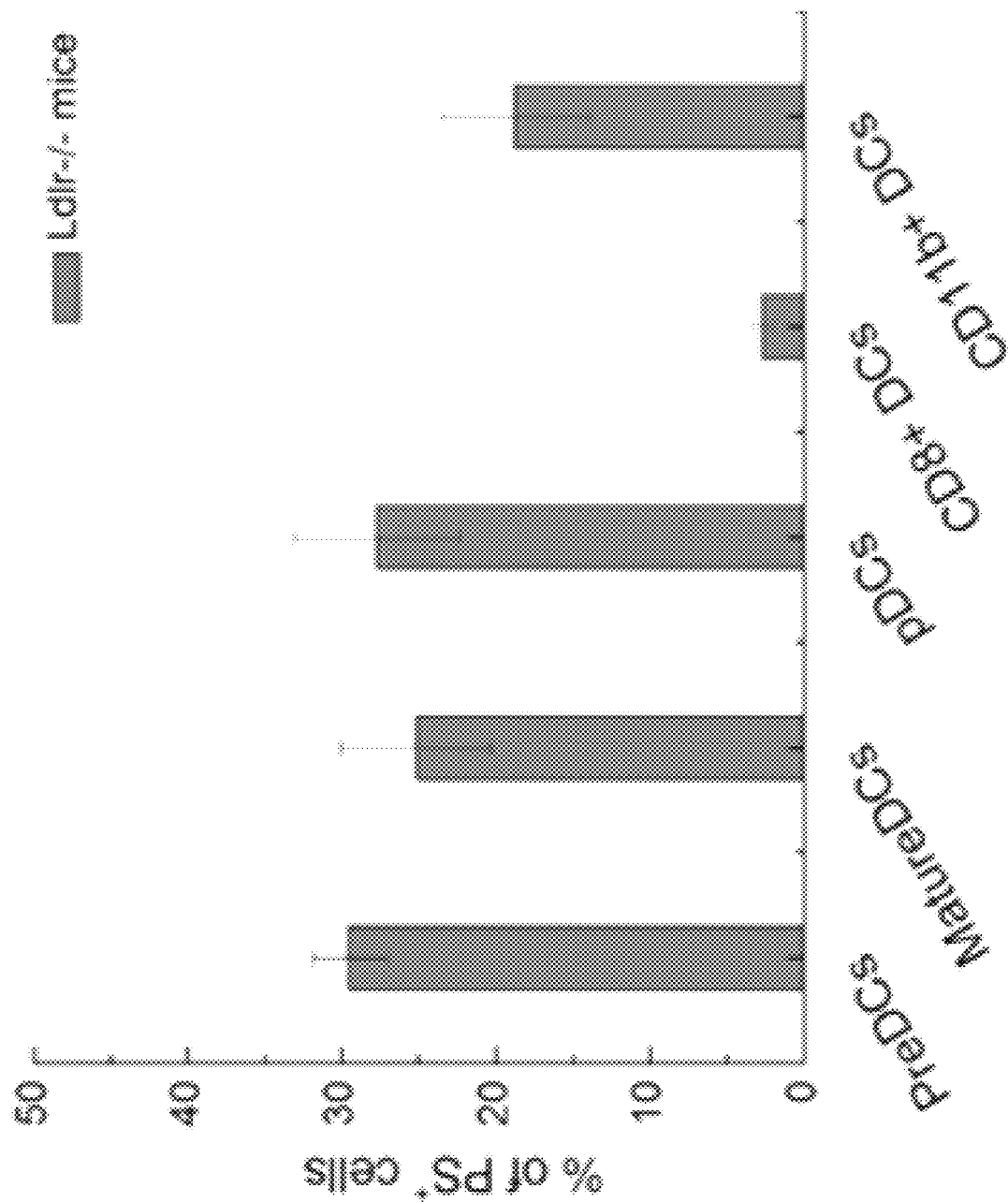
FIG. 13 Polymersome biodistributions within dendritic cell subsets in aortas of atherosclerotic mice. Aorta 24 h after I.V. injection were analyzed by flow cytometry. Histograms show the average percentages±standard deviation (SD) of polymersome positive (PS$^+$) cells for each indicated cell. PreDCs: I-A/I-E-CD11c$^+$; mature DCs: I-A/I-E$^+$CD11c$^+$; plasmacytoid DCs: I-A/I-E$^+$CD11c$^+$Gr-1$^+$B220$^+$; CD8$^+$ DCs: I-A/I-E$^+$CD11c$^+$CD8$^+$; CD11b$^+$ DCs: I-A/I-E$^+$CD11c$^+$CD11b$^+$. N=3 in each group, two independent experiments.

PS+), with the exception of CD8+ DC, which are typically non-migratory and restricted to lymphoid organs (FIG. 13) [32, 34].

To further verify the targeting of DC by PS in aorta, Applicant performed immunofluorescence studies of aorta from naïve C57BL/6 mice and Ldlr$^{-/-}$ mice 24 h after injection with DyLight 650-labeled PS. Cross-sectional histology stained with DAPI and Alexa-488 conjugated CD11c antibody was observed under spinning disk confocal microscopy. CD11c is a key marker of DC, and a significant increase in the number of CD11c+ cells were detected in the intimal region of Ldlr$^{-/-}$ aortic lesions, while minimal CD11c+ cells were observed in the aorta of control mice (FIG. 7C, D). Furthermore, PS were found to accumulate extensively in the lamina adventitia of only the Ldlr$^{-/-}$ mice. In FIG. 7B, Z-stacks showed that fluorescence from both the PS (red) and CD11c+ DC (green) was seen in the intima, which further demonstrated the targeting effects of PS to DC in the aortic lesion of Ldlr$^{-/-}$ mice. These results indicated that in the absence of surface conjugated targeting ligands, the PS morphology was sufficient to enhance targeting of aortic DC in atherosclerotic mice. The localization of PS within the aorta to primarily the adventitia, suggests that the PS may enter arterial lesions via the vasa vasorum, which is consistent with the proposed mechanism used by other nanomaterials to enter and image atherosclerotic plaques [44].

Conclusion

Conjugation of a targeting ligand to the surface of a nanomaterial typically results in only an incremental improvement in specificity, as this strategy cannot influence non-specific uptake by the MPS. Applicant demonstrates here that changing the nanostructure morphology, while maintaining the same surface chemistry, can significantly impact both non-specific and specific uptake by inflammatory cell subsets as a function of both time and disease state. Switching from a MC to a PS morphology resulted in a decrease in uptake by liver macrophages by over 50% while improving the targeting of splenic DC by up to 35%. Liver-resident macrophages represent the largest MPS population, and decreasing their uptake can significantly improve therapeutic targeting. Applying NSET under the diseased condition of atherosclerosis resulted in several additional advantages that may improve diagnosis and immunotherapeutic treatment of heart disease. The PS morphology enhanced the specificity of targeting DC in both spleen and aortic plaques, with the added benefit of targeting Ly6C+ monocytes in the blood that accelerate the progression of CVD. These differences in endocytosis likely reflect complex atherosclerosis-related changes in cell activation state, surface receptor expression, preferred mechanisms of endocytosis, and lipid content in biological fluids. These results demonstrate that nanostructure morphology and systemic abnormalities due to disease state deserve equal attention as surface chemistry when designing nanomaterials for therapeutic delivery.

Materials and Methods

Materials

All chemicals were purchased from Sigma-Aldrich, unless otherwise stated. Antibodies, Zombie Aqua fixable cell viability kit, cell staining buffer and cell fixation buffer were purchased from BioLegend.

Synthesis of PEG-bl-PPS Block Copolymers

Distinct NS were fabricated based on the controlled self-assembly of poly (ethylene glycol)-bl-poly (propylene sulfide) (PEG-bl-PPS) block copolymers. A variety of different architectures can be obtained by controlling the molecular weight (MW) ratio of the hydrophilic PEG to hydrophobic PPS blocks. Block copolymers PEGm-bl-PPSn were synthesized as previously described [45]. Briefly, PEG thioacetate initiator was deprotected by sodium methoxide to reveal the initiating thiolate. Propylene sulfide (PS) was added as necessary to polymerize the desired block lengths, and the polymerization was end-capped by 2,2'-Dithiodipyridine or protonated with $CH_3COOH$ to create the PPS thiol-end groups for subsequent fluorophore conjugation. The obtained block copolymers ($PEG_{17}$-bl-$PPS_{30}$, $PEG_{45}$-bl-$PPS_{20}$, and $PEG_{45}$-bl-$PPS_{44}$) were purified by double precipitation in cold diethyl ether or methanol, and then characterized by $^1H$ NMR ($CDCl_3$) and gel permeation chromatography (GPC) (ThermoFisher Scientific) using Waters Styragel THF columns with refractive index and UV-Vis detectors in a tetrahydrofuran (THF) mobile phase.

Assembly of PEG-bl-PPS Nanostructures and Loading with ICG

Three different NS: $PEG_{45}$-bl-PPS20 micelles (MC), $PEG_{17}$-bl-$PPS_{30}$ polymersomes (PS), and $PEG_{45}$-bl-$PPS_{44}$ filomicelles (FM) were assembled and loaded with the lipophilic near infrared (NIR) fluorescence imaging agent indocyanine green (ICG) using the thin film hydration method as previously described [46]. Briefly, 8.6 mM of each block copolymer was dissolved in 150 µl dichloromethane within 1.8 mL clear glass vials (ThermoFisher Scientific). After desiccation to remove the solvent, the resulting thin films were hydrated in 1 mL of phosphate-buffered saline (PBS) or 1 mL of ICG solution (0.258 mM in PBS solution) under shaking at 1500 rpm overnight. The single layer PS were obtained by extrusion multiple times through 0.2 µm and then 0.1 µm nucleopore track-etched membranes (Whatman). The ICG-loaded NS were purified from free ICG by Zeba Spin Desalting Columns (7K MWCO, ThermoFisher Scientific) equilibrated with PBS solution and dialyzed against PBS using Slide-A-Lyzer Dialysis Cassettes (7K MWCO, ThermoFisher Scientific).

Covalent Fluorescent Labeling of PEG-bl-PPS Nanostructures

Maleimide-functionalized fluorescent dye was conjugated to NS via free thiol-end functionalized moieties on the PPS core. Block copolymers protonated with $CH_3COOH$ were first assembled into nanostructures using thin film hydration in PBS as previously described. Solutions of MC, PS and FM at 30 mg/ml were covalently labeled with 0.07 mM of DyLight 650-maleimide (Fisher) under shaking at room temperature for 12 h. Excess unreacted DyLight 650-maleimide was removed by Zeba Spin Desalting Columns (7K MWCO) equilibrated with PBS solution and dialysis against PBS using Slide-A-Lyzer Dialysis Cassettes (7K MWCO, ThermoFisher Scientific). The degree of fluorescence labeling was determined by diluting samples in PBS solution and measuring the fluorescence in a spectrophotometer (SpectraMax M3, Molecular Devices). The degree of DyLight 650 labeling for various nanomaterials was: 0.100 µg/mg for MC, 0.067 µg/mg for PS, and 0.073 µg/mg for FM.

Characterization of PEG-bl-PPS Nanostructures

The size distribution and zeta potential of the nanostructures were analyzed by Zetasizer Nano (Malvern Instruments) with a 4 mW He—Ne 633 nm laser at 1 mg/mL in PBS. The morphology of each nanostructure were determined by cryogenic electron microscopy (CryoTEM). The ICG concentration of different nanoparticles was measured by UV-Vis spectroscopy (SpectraMax M3, Molecular Devices) after sample dilution in PBS solution. To characterize the stability and fluorescent properties of ICG-loaded NS, different molar ratios of polymer: ICG (1:10, 1:25, 1:33, 1:50, 1:75 and 1:100) were prepared with 10 mg/ml of PEG-bl-PPS. Solutions of ICG-loaded NS were diluted 1:50 in PBS solution prior to the generation of the absorbance spectrum. Wavelengths from 250 nm to 850 nm were scanned with 10 nm increments. The fluorescent spectrum was measured by the excitation of 780 nm and emission from 700 nm to 850 nm with 5 nm increments. In all cases, ICG-loaded NS were matched with free ICG (in PBS solution) at the same concentrations of ICG. Before animal studies, all samples were verified to be endotoxin-free (<0.01 EU/mg) by the TLR4 activation HEK Blue LPS detection assay (Invivogen).

Animals

C57BL/6 female mice, 6-8 weeks old, were purchased from Jackson Laboratories. The low density lipoprotein (LDL) receptor-deficient mice ($Ldlr^{-/-}$ mice) with C57BL/6 background were obtained from The Jackson Laboratory at 4 weeks old and fed a high-fat diet (HFD, Harlan Teklad TD.88137, 42% kcal from fat) starting at 6 weeks old for 16 weeks until sacrificed. The control diet for naïve mice was TD.08485 with 13% kcal from fat. All mice were housed and maintained in the Center for Comparative Medicine at Northwestern University. All animal experimental procedures were performed according to protocols approved by the Northwestern University Institutional Animal Care and Use Committee (IACUC).

Assessment of Organ-Level Biodistributions of PEG-bl-PPS Nanostructures in Naïve Mice The ICG-loaded MC, PS and FM were prepared with the optimal molar ratio of PEG-bl-PPS:ICG (33:1) and suspended in PBS. Free ICG (50 µg/mL in PBS solution) served as a control. C57BL/6 mice (n=6) were injected intravenously with 150 µl of free ICG, MC, PS and FM (7.5 µg of loaded ICG in each sample). At different time points (1 h, 24 h, and 48 h post-injection), whole-body NIR fluorescence imaging was performed using an IVIS Lumina (Center for Advanced Molecular Imaging, Northwestern University) with $\lambda_{exc}$=745 nm, $\lambda_{em}$=810 nm, exposure time=2 s and f/stop=2. For organ NIR fluorescence imaging, animals were euthanized by carbon dioxide and liver, spleen, kidney, heart, and lung were harvested in petri dishes and imaged by the IVIS Lumina with the same parameters as previous.

Immune Cell Biodistributions of PEG-Bl-PPS Nanostructures in Naïve Mice

C57BL/6 female mice (n=6-8), were injected intravenously with 150 µl of MC, PS, and FM with block copolymer concentration of 15 mg/mL. At different time points (1 h, 24 h, and 48 h post-injection), mice were anesthetized by intraperitoneal (i.p.) injection of a mixture of Ketamine/Xylazine followed by exsanguination. Blood was collected by retro-orbital puncture with BD Microtainer tubes and dipotassium EDTA (BD Biosciences). Serum was separated by centrifugation at 3000 rpm at 4° C. for 25 min. Fluorescence intensity of each nanostructure was normalized by diluting NS solutions in PBS and measuring the fluorescence using a spectrophotometer. The fluorescence of blood serum was measured with an excitation of 655 nm and the emission of 675 nm and correlated with the normalized standard curve for each DyLight 650-labeled NS. To prepare white blood cell suspensions, blood cells were washed twice with 10 ml PBS and treated 3× with ammonium-chloride-potassium (ACK) lysis buffer (Invivogen) to eliminate red blood cells. Liver, spleen, LN (popliteal, inguinal, axillary and brachial), and kidneys were harvested, gently dissociated and incubated in a 12-well plate with each well of 2 ml Collagenase D (2 mg/mL) for 45 min at 37° C. and 5% CO2. Single-cell suspensions were prepared by mechanical dissociation and passing through a 70 µm cell strainer. Anti-mouse CD16/CD32 was used to block FcRs and Zombie Aqua fixable viability dye was used to determine live/dead cells. For flow cytometric analysis, cells were stained using cocktails of fluorophore-conjugated anti-mouse antibodies: panel 1: CD45-FITC, CD3-APC/Cy7, CD4-PE, CD8α-PE/Cy7, NK1.1-PerCP-Cy5.5, CD19-Pacific Blue; panel 2: I-A/I-E-FITC, CD11c-Pacific Blue, CD8α-PE/Cy7, CD11b-PerCP-Cy5.5, CD45RB/B220-PE, Gr-1-APC/Cy7; and panel 3: F4/80-FITC, CD11c-Pacific Blue, CD11b-PerCP-Cy5.5, Ly6C-APC/Cy7, Ly6G-PE/Cy7. After washes, cells were fixed by IC cell fixation buffer (Biosciences). Flow cytometry was performed with FACSDiva on a LSRII flow cytometer (BD Biosciences) and data were analyzed with FlowJo software.

Assessment of PEG-bl-PPS Nanostructure Biodistributions in Atherosclerotic Mice $Ldlr^{-/-}$ mice fed a HFD for 16 weeks were used as a model of atherosclerosis. The $Ldlr^{-/-}$ mice (n=8) were administered 150 µl of PS at a concentration of 15 mg/ml via tail vein injection. Blood was drawn by retro-orbital bleeding and organs (spleen, LNs, liver and kidneys) were collected at 24 h post-injection. Aortas were carefully harvested after perfusion with PBS solution under a microscope. To prepare single cell suspension, the aortic tissue was cut into small pieces and digested in Aorta Dissociation Enzyme Solution (ADES) (125 U/ml collagenase type X1, 60 U/ml hyaluronidase type 1-s, 60 U/ml DNase I, and 450 U/ml collagenase type I, in 2.5 mL of RPMI-1640 medium without FBS, modified from [47]) for 1 hour at 37° C. and 5% CO2. The other organs were dissociated and digested with collagenase D (2 mg/mL) as described above. Single-cell suspensions were obtained by mechanical dissociation and passing through a 70 µm cell strainer. FcRs were blocked with anti-mouse CD16/CD32 and cells stained with Zombie Aqua fixable viability dye prior to antibody staining. Cells were then stained with multiple cocktails of fluorophore-conjugated anti-mouse antibodies as described above. Samples were analyzed by Flow cytometer and FlowJo software. The gating strategy to identify the immune cell subsets and percentages of NS positive (NS+) cells is depicted in FIG. 11. The NS without a fluorescent label were set as negative control gates in the analysis.

Immunofluorescence $Ldlr^{-/-}$ mice and C57BL/6 naïve mice (as controls) were injected intravenously with 150 µl of PS (15 mg/ml) as previously described. After 24 h, the heart and aorta were perfused with 4% paraformaldehyde (PFA)/5% sucrose in PBS solution for 10 min. The aorta was harvested and fixed in 4% PFA/5% sucrose PBS solution 12 h at 4° C. The isolated aortic arch-derived arteries were immersed in 15% sucrose solution for 12 h and then 30% sucrose solution for 24 h. The resulting specimens were embedded in Tissue-Tek OCT and frozen at −80° C. Tissue blocks were sectioned at 5 µm thickness and stained with 4',6-diamidino-2-phenylindole (DAPI) and Alex-488-anti-CD11c antibody. Images were taken on a spinning disk confocal microscope (Leica). Z-stacks were performed at the inner aortic tissue at 63× magnification using MetaMorph software.

Statistical Analysis

A minimum of two independent experiments were studied, with 3-5 mice per treatment group in each experiment. Two-tail Student T-tests were performed to determine statistical significance.

REFERENCES

1. Haniffa, M., V. Bigley, and M. Collin, *Human mononuclear phagocyte system reunited.* Semin Cell Dev Biol, 2015. 41: p. 59-69.

2. Palombo, M., et al., *Pharmaceutical and toxicological properties of engineered nanomaterials for drug delivery.* Annu Rev Pharmacol Toxicol, 2014. 54: p. 581-98.
3. Rossman, J. S., G. P. Leser, and R. A. Lamb, *Filamentous influenza virus enters cells via macropinocytosis.* J Virol, 2012. 86(20): p. 10950-60.
4. Gao, H., W. Shi, and L. B. Freund, *Mechanics of receptor-mediated endocytosis.* Proc Natl Acad Sci USA, 2005. 102(27): p. 9469-74.
5. Nel, A. E., et al., *Understanding biophysicochemical interactions at the nano-bio interface.* Nat Mater, 2009. 8(7): p. 543-57.
6. Duan, X. and Y. Li, *Physicochemical Characteristics of Nanoparticles Affect Circulation, Biodistribution, Cellular Internalization, and Trafficking.* Small, 2013. 9(9-10): p. 1521-1532.
7. Geng, Y., et al., *Shape effects of filaments versus spherical particles inflow and drug delivery.* Nat Nanotechnol, 2007. 2(4): p. 249-55.
8. Stano, A., et al., *Tunable T cell immunity towards a protein antigen using polymersomes vs. solid-core nanoparticles.* Biomaterials, 2013. 34(17): p. 4339-46.
9. Hubbell, J. A., S. N. Thomas, and M. A. Swartz, *Materials engineering for immunomodulation.* Nature, 2009. 462(7272): p. 449-60.
10. Moon, J. J., B. Huang, and D. J. Irvine, *Engineering nano-and microparticles to tune immunity.* Adv Mater, 2012. 24(28): p. 3724-46.
11. Allen, S., Y. G. Liu, and E. Scott, *Engineering nanomaterials to address cell-mediated inflammation in atherosclerosis.* Regen Eng Transl Med, 2016. 2(1): p. 37-50.
12. Writing Group, M., et al., *Heart Disease and Stroke Statistics-2016 Update: A Report From the American Heart Association.* Circulation, 2016. 133(4): p. e38-60.
13. Getz, G. S., P. A. Vanderlaan, and C. A. Reardon, *Natural killer T cells in lipoprotein metabolism and atherosclerosis.* Thromb Haemost, 2011. 106(5): p. 814-9.
14. Paulson, K. E., et al., *Resident intimal dendritic cells accumulate lipid and contribute to the initiation of atherosclerosis.* Circ Res, 2010. 106(2): p. 383-90.
15. Simon, D. I. and D. Zidar, *Neutrophils in atherosclerosis: alarmin evidence of a hit and run?* Circ Res, 2012. 110(8): p. 1036-8.
16. Takeuchi, O. and S. Akira, *Pattern recognition receptors and inflammation.* Cell, 2010. 140(6): p. 805-20.
17. Jongstra-Bilen, J., et al., *Low-grade chronic inflammation in regions of the normal mouse arterial intima predisposed to atherosclerosis.* J Exp Med, 2006. 203(9): p. 2073-83.
18. Gautier, E. L., et al., *Conventional dendritic cells at the crossroads between immunity and cholesterol homeostasis in atherosclerosis.* Circulation, 2009. 119(17): p. 2367-75.
19. Weber, C., et al., *CCL17-expressing dendritic cells drive atherosclerosis by restraining regulatory T cell homeostasis in mice.* J Clin Invest, 2011. 121(7): p. 2898-910.
20. Niessner, A. and C. M. Weyand, *Dendritic cells in atherosclerotic disease.* Clin Immunol, 2010. 134(1): p. 25-32.
21. Van de Broek, B., et al., *Specific cell targeting with nanobody conjugated branched gold nanoparticles for photothermal therapy.* ACS Nano, 2011. 5(6): p. 4319-28.
22. Swartz, M. A., S. Hirosue, and J. A. Hubbell, *Engineering Approaches to Immunotherapy.* Science Translational Medicine, 2012. 4(148): p. 148rv9-148rv9.
23. Irvine, D. J., et al., *Synthetic Nanoparticles for Vaccines and Immunotherapy.* Chem Rev, 2015. 115(19): p. 11109-46.
24. Kirchherr, A.-K., A. Briel, and K. Mäder, *Stabilization of Indocyanine Green by Encapsulation within Micellar Systems.* Molecular Pharmaceutics, 2009. 6(2): p. 480-491.
25. Scott, E. A., et al., *Dendritic cell activation and T cell priming with adjuvant-and antigen-loaded oxidation-sensitive polymersomes.* Biomaterials, 2012. 33(26): p. 6211-9.
26. Vasdekis, A. E., et al., *Precision intracellular delivery based on optofluidic polymersome rupture.* ACS Nano, 2012. 6(9): p. 7850-7.
27. Kirchherr, A. K., A. Briel, and K. Mader, *Stabilization of indocyanine green by encapsulation within micellar systems.* Mol Pharm, 2009. 6(2): p. 480-91.
28. Tunon, M. J., et al., *Liver blood flow changes during laparoscopic surgery in pigs. A study of hepatic indocyanine green removal.* Surg Endosc, 1999. 13(7): p. 668-72.
29. Kim, T. H., et al., *Filamentous, Mixed Micelles of Triblock Copolymers Enhance Tumor Localization of Indocyanine Green in a Murine Xenograft Model.* Molecular Pharmaceutics, 2012. 9(1): p. 135-143.
30. Champion, J. A. and S. Mitragotri, *Role of target geometry in phagocytosis.* Proceedings of the National Academy of Sciences of the United States of America, 2006. 103(13): p. 4930-4934.
31. Racanelli, V. and B. Rehermann, *The liver as an immunological organ.* Hepatology, 2006. 43(S1): p. S54-S62.
32. Mildner, A. and S. Jung, *Development and Function of Dendritic Cell Subsets.* Immunity, 2014. 40(5): p. 642-656.
33. Merad, M., et al., *The dendritic cell lineage: ontogeny and function of dendritic cells and their subsets in the steady state and the inflamed setting.* Annu Rev Immunol, 2013. 31: p. 563-604.
34. Joffre, O. P., et al., *Cross-presentation by dendritic cells.* Nat Rev Immunol, 2012. 12(8): p. 557-569.
35. Doring, Y., et al., *Auto-antigenic protein-DNA complexes stimulate plasmacytoid dendritic cells to promote atherosclerosis.* Circulation, 2012. 125(13): p. 1673-83.
36. Daissormont, I. T., et al., *Plasmacytoid dendritic cells protect against atherosclerosis by tuning T-cell proliferation and activity.* Circ Res, 2011. 109(12): p. 1387-95.
37. Platt, C. D., et al., *Mature dendritic cells use endocytic receptors to capture and present antigens.* Proc Natl Acad Sci USA, 2010. 107(9): p. 4287-92.
38. Reizis, B., et al., *Plasmacytoid Dendritic Cells: Recent Progress and Open Questions.* Annual review of immunology, 2011. 29: p. 163-183.
39. Weber, C. and H. Noels, *Atherosclerosis: current pathogenesis and therapeutic options.* Nat Med, 2011. 17(11): p. 1410-1422.
40. Swirski, F. K. and M. Nahrendorf, *Leukocyte Behavior in Atherosclerosis, Myocardial Infarction, and Heart Failure.* Science, 2013. 339(6116): p. 161-166.
41. Swirski, F K., et al., *Ly-6Chi monocytes dominate hypercholesterolemia-associated monocytosis and give rise to macrophages in atheromata.* J Clin Invest, 2007. 117(1): p. 195-205.
42. Alitalo, K., *The lymphatic vasculature in disease.* Nat Med, 2011. 17(11): p. 1371-80.
43. Bobryshev, Y. V, *Dendritic cells and their role in atherogenesis.* Lab Invest, 2010. 90(7): p. 970-984.

44. Lobatto, M. E., et al., *Atherosclerotic plaque targeting mechanism of long-circulating nanoparticles established by multimodal imaging.* ACS Nano, 2015. 9(2): p. 1837-47.
45. Cerritelli, S., et al., *Aggregation Behavior of Poly (ethylene glycol-bl-propylene sulfide) Di-and Triblock Copolymers in Aqueous Solution.* Langmuir, 2009. 25(19): p. 11328-11335.
46. Scott, E. A., et al., *Dendritic cell activation and T cell priming with adjuvant-and antigen-loaded oxidation-sensitive polymersomes.* Biomaterials, 2012. 33(26): p. 6211-6219.
47. Butcher, M. J., et al., *Flow cytometry analysis of immune cells within murine aortas.* J Vis Exp, 2011(53).

3. The method of claim 1, wherein the size of the polymersome is about 90 to about 150 nm in diameter, and wherein the statin is delivered to dendritic cells within the blood vessels of the subject and ameliorates at least one symptom of cardiovascular disease.

4. The method of claim 1, wherein the cardiovascular disease comprises atherosclerotic lesions.

5. The method of claim 1, wherein the polymersome does not contain a targeting ligand specific for dendritic cells.

6. The method of claim 1, wherein the polymersomes increase the specific uptake of an agent by dendritic cells within the blood vessels by at least 20% as compared to the agent alone.

The invention claimed is:

1. A method of targeting an agent to dendritic cells in a subject having or suspected of having cardiovascular disease, the method comprising
administering to the subject a polymersome comprising block copolymers of polyethylene glycol) (PEG) and polypropylene sulfide) (PPS) incorporating or encapsulating a statin for the diagnosis or treatment of cardiovascular disease, wherein the polymersome targets dendritic cells within the subject.

2. The method of claim 1, wherein the polymersome comprises a vesicular polymer membrane comprising $PEG_{17}$-bl-$PPS_{30}$.

7. The method of claim 1, the method further comprising:
selecting a subject having or suspected of having atherosclerotic lesions prior to the administering step.

8. A method of targeting an agent to dendritic cells within atherosclerotic lesions in a subject having or suspected of having atherosclerotic lesions, the method comprising
administering to the subject a polymersome comprising block copolymers of poly(ethylene glycol) (PEG) and polypropylene sulfide) (PPS), the polymersome incorporating or encapsulating a statin for the diagnosis or treatment of atherosclerotic lesions, wherein the polymersome targets dendritic cells within the subject.

9. The method of claim 8, wherein the polymersome comprises $PEG_{17}$-bl-$PPS_{30}$.

10. The method of claim 8, wherein the size of the polymersome is about 90 to about 150 nm in diameter, and wherein the agent is delivered to dendritic cells within the blood vessels of the subject and ameliorates at least one symptom of cardiovascular disease.

\* \* \* \* \*

UNITED STATES PATENT AND TRADEMARK OFFICE
CERTIFICATE OF CORRECTION

PATENT NO. : 10,821,078 B2
APPLICATION NO. : 15/637333
DATED : November 3, 2020
INVENTOR(S) : Evan A. Scott, Sijia Yi and Sean D. Allen Page 1 of 1

It is certified that error appears in the above-identified patent and that said Letters Patent is hereby corrected as shown below:

In the Claims

Column 27, Line 5, "agent" should be --statin--.

Signed and Sealed this
Third Day of August, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 3

<210> SEQ ID NO 1
<211> LENGTH: 19
<212> TYPE: PRT
<213> ORGANISM: Homo sapiens

<400> SEQUENCE: 1

Thr Arg Phe Lys His Leu Arg Lys Tyr Thr Tyr Asn Tyr Glu Ala Glu
1               5                   10                  15

Ser Ser Ser

<210> SEQ ID NO 2
<211> LENGTH: 20
<212> TYPE: PRT
<213> ORGANISM: Homo sapiens

<400> SEQUENCE: 2

Ile Ala Leu Asp Asp Ala Lys Ile Asn Phe Asn Glu Lys Leu Ser Gln
1               5                   10                  15

Leu Gln Thr Tyr
            20

<210> SEQ ID NO 3
<211> LENGTH: 20
<212> TYPE: PRT
<213> ORGANISM: Homo sapiens

<400> SEQUENCE: 3

Lys Thr Thr Lys Gln Ser Phe Asp Leu Ser Val Lys Ala Gln Tyr Lys
1               5                   10                  15

Lys Asn Lys His
            20
```